United States Patent [19]

Belinka, Jr. et al.

[11] Patent Number: 5,449,761

[45] Date of Patent: Sep. 12, 1995

[54] METAL-BINDING TARGETED POLYPEPTIDE CONSTRUCTS

[75] Inventors: Benjamin A. Belinka, Jr., Kendall Park; Daniel J. Coughlin, Robbinsville, both of N.J.; Vernon L. Alvarez, Morrisville, Pa.; Richard Wood, Rocky Hill, N.J.

[73] Assignee: Cytogen Corporation, Princeton, N.J.

[21] Appl. No.: 127,351

[22] Filed: Sep. 28, 1993

[51] Int. Cl.⁶ .................. C07C 337/06; C07C 335/16; A61K 38/00

[52] U.S. Cl. ........................ 534/10; 534/14; 534/15; 530/300; 530/326; 530/327; 530/328; 530/399; 530/408; 564/18; 564/23; 564/26; 564/27; 564/28

[58] Field of Search ............ 530/328, 391.5, 399, 530/402, 300, 408, 326, 327; 514/15, 16; 424/1.45, 1.69; 534/10, 14, 15, 16; 564/18, 23, 26, 27, 28

[56] References Cited

U.S. PATENT DOCUMENTS

| | | | |
|---|---|---|---|
| 4,048,326 | 9/1977 | Berg et al. | 424/300 |
| 4,060,636 | 11/1977 | Kilbourn et al. | |
| 4,086,235 | 4/1978 | Beard | |
| 4,287,362 | 9/1981 | Yokoyama et al. | |
| 4,559,221 | 12/1985 | Arano et al. | 424/1.1 |
| 4,666,697 | 5/1987 | Takahashi et al. | 424/1.1 |
| 4,732,864 | 3/1988 | Tolman | |
| 5,080,884 | 1/1992 | McBride et al. | |
| 5,101,041 | 3/1992 | Troutner et al. | |
| 5,135,737 | 8/1992 | Keana | 424/9 |
| 5,196,510 | 3/1993 | Rodwell et al. | |
| 5,206,370 | 4/1993 | Schwartz et al. | 546/281 |
| 5,276,140 | 1/1994 | Nitecki et al. | 530/391.1 |
| 5,326,856 | 7/1994 | Coughlin et al. | 534/14 |

FOREIGN PATENT DOCUMENTS

| | | |
|---|---|---|
| 0188256 | 7/1986 | European Pat. Off. |
| 0306168 | 3/1989 | European Pat. Off. |
| 1307250 | 2/1973 | United Kingdom |
| WO90/06323 | 6/1990 | WIPO |
| WO91/01144 | 2/1991 | WIPO |
| WO92/13572 | 8/1992 | WIPO |

OTHER PUBLICATIONS

Int. J. Nucl. Med. Biol., vol. 12, No. 6, pp. 425–430, Yashushi Arano, et al., "Synthesis And Evaluation Of A New Bifunctional Chelating Agent For 99m Tc Labeling Proteins: p-Carboxyethyl-Phenylglyoxaldi(-N-Methylthiosemicarbazone)".

(List continued on next page.)

*Primary Examiner*—Gary L. Geist
*Assistant Examiner*—Lara E. Chapman
*Attorney, Agent, or Firm*—Lowe, Price, LeBlanc & Becker

[57] ABSTRACT

This invention relates to the preparation and use of novel open-chain or cyclic polypeptide constructs in which two or more polypeptide chains, in an open-chain construct, or one or more chains, in a cyclic construct, are chemically derivatized such that the resulting construct exhibits both metal-binding capability and tissue-, organ- or cell-targeting selectivity. In particular, the polypeptide constructs of the present invention comprise compounds of the formula (I):

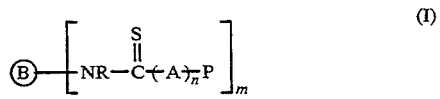

(I)

in which, "B" is a hydrocarbon backbone, "P" is a polypeptide capable of targeting particular cells, tissues or organs of the body, "A" may be the group —NR'—NR"— or the group —NR'—NR"—L— in which L may be an aliphatic or aromatic linker group, R, R' and R" may be the same or different and may be hydrogen or an aliphatic group, m is an integer $\geq 2$, provided that the groups R, R', R', L and "P" of a given chain may be the same or different from the groups R, R', R", L and "P" of another chain, n is an integer $\geq 0$; or a pharmaceutically acceptable salt thereof. The constructs of the present invention are capable of binding a variety of metallic species.

21 Claims, 2 Drawing Sheets

OTHER PUBLICATIONS

The Lancet, Feb. 4, 1989, E. P. Krenning, et al., "Localisation Of Endocrine-Related Tumours With Radioiodinated Analogue Of Somatostatin", pp. 242–244.

The Journal of Nuclear Medicine, vol. 31, No. 9, Sep. 1990, Willem H. Bakker, et al., "Receptor Scintigraphy With A Radioiodinated Somatostatin Analogue: Radiolabeling, Purification, Biologic Activity, And In Vivo Application In Animals", pp. 1501–1509.

The New England Journal of Medicine, vol. 323, No. 18, S. W. J. Lamberts, et al., Nov. 1, 1990, "Somatostatin-Receptor Imaging In The Localization Of Endocrine Tumors", pp. 1246–1249.

Journal of Medicinal Chemistry, vol. 35, No. 2, Jan. 24, 1992, Ernest Cullen, et al., "BIS Basic Substituted Diaminobenzobisthiazoles As Potential Antiarthritic Agents", pp. 350–361.

Journal of Chemical Education, vol. 62, No. 11, Nov. 1985, Thomas C. Pinkerton, et al., "Bioinorganic Activity Of Technetium Radiopharmaceuticals", pp. 965–973.

Radiochem. Radioanal. Letters 29(4), pp. 171–178, 1977, R. Kopunec, et al., "Reaction Of Pertechnetate With Thiourea In The Nitric Acid Solutions".

The Journal of Nuclear Medicine, vol. 28, No. 6, Jun. 1987, Yasushi Arano, et al., "Technetium-99m-Labeled Monoclonal Antibody With Preserved Immunoreactivity And High In Vivo Stability", pp. 1027–1033.

Cullen et al., J. Med. Chem., vol. 35(2), Jan. 24, 1992, pp. 350–361.

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:1:

```
Gly  Asn  His  Trp  Ala  Val  Gly  His  Leu  Met
1                  5                       10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:2:

```
Gly  Asn  Leu  Trp  Ala  Thr  Gly  His  Phe  Met
1                  5                       10
```

( 2 ) INFORMATION FOR SEQ ID NO:3:

( i ) SEQUENCE CHARACTERISTICS:

(A) LENGTH: 17 amino acids
(B) TYPE: amino acid
(D) TOPOLOGY: unknown (ii) MOLECULE TYPE: peptide (xi) SEQUENCE DESCRIPTION: SEQ ID NO:3:

Leu Glu Gly Pro Trp Leu Phe Glu Glu Glu Ala Tyr Gly Trp Met Asp
1               5                   10                  15
Gly (2) INFORMATION FOR SEQ ID NO:4:

(i) SEQUENCE CHARACTERISTICS:
    (A) LENGTH: 6 amino acids
    (B) TYPE: amino acid
    (D) TOPOLOGY: unknown (ii) MOLECULE TYPE: peptide (xi) SEQUENCE DESCRIPTION: SEQ ID NO:4:

Ile Lys Val Ala Val Ser
1               5

(2) INFORMATION FOR SEQ ID NO:5:

(i) SEQUENCE CHARACTERISTICS:
    (A) LENGTH: 5 amino acids
    (B) TYPE: amino acid
    (D) TOPOLOGY: unknown (ii) MOLECULE TYPE: peptide (xi) SEQUENCE DESCRIPTION: SEQ ID NO:5:

Tyr Ile Gly Ser Arg
1               5

(2) INFORMATION FOR SEQ ID NO:6:

(i) SEQUENCE CHARACTERISTICS:
    (A) LENGTH: 10 amino acids
    (B) TYPE: amino acid
    (D) TOPOLOGY: unknown (ii) MOLECULE TYPE: peptide (ix) FEATURE:
    (A) NAME/KEY: Modified-site
    (B) LOCATION: 6
    (D) OTHER INFORMATION: /note="Position 6 may be either
        Gly or D-Trp."

(xi) SEQUENCE DESCRIPTION: SEQ ID NO:6:

Glu His Trp Ser Tyr Xaa Leu Arg Pro Gly
1               5                   10

(2) INFORMATION FOR SEQ ID NO:7:

(i) SEQUENCE CHARACTERISTICS:
    (A) LENGTH: 14 amino acids
    (B) TYPE: amino acid
    (D) TOPOLOGY: unknown (ii) MOLECULE TYPE: peptide (ix) FEATURE:
    (A) NAME/KEY: Modified-site
    (B) LOCATION: 7
    (D) OTHER INFORMATION: /note="Position 7 may be Phe or
        Tyr."

(xi) SEQUENCE DESCRIPTION: SEQ ID NO:7:

```
        Ala  Gly  Cys  Lys  Asn  Phe  Xaa  Trp  Lys  Thr  Phe  Thr  Ser  Cys
        1              5                        10
```

( 2 ) INFORMATION FOR SEQ ID NO:8:

( i ) SEQUENCE CHARACTERISTICS:
        ( A ) LENGTH: 30 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:8:

```
        Gly  Pro  Glu  Thr  Leu  Cys  Gly  Ala  Glu  Leu  Val  Asp  Ala  Ala  Leu  Gln
        1              5                        10                            15

Phe  Val  Cys  Gly  Asp  Arg  Gly  Phe  Tyr  Phe  Asn  Lys  Pro  Thr
                        20                        25                        30
```

( 2 ) INFORMATION FOR SEQ ID NO:9:

( i ) SEQUENCE CHARACTERISTICS:
        ( A ) LENGTH: 33 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:9:

```
        Gly  Pro  Glu  Thr  Leu  Cys  Gly  Ala  Glu  Leu  Val  Asp  Ala  Ala  Leu  Gln
        1              5                        10                            15

Phe  Val  Cys  Gly  Asp  Arg  Gly  Phe  Tyr  Phe  Asn  Lys  Pro  Thr  Gly  Tyr
                        20                        25                        30

Gly
```

( 2 ) INFORMATION FOR SEQ ID NO:10:

( i ) SEQUENCE CHARACTERISTICS:
        ( A ) LENGTH: 24 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:10:

```
        Asn  Asp  Lys  Ile  Pro  Val  Ala  Leu  Gly  Leu  Lys  Glu  Lys  Asn  Leu  Tyr
        1              5                        10                            15

Leu  Ser  Cys  Val  Leu  Lys  Asp  Asp
                        20
```

( 2 ) INFORMATION FOR SEQ ID NO:11:

( i ) SEQUENCE CHARACTERISTICS:
        ( A ) LENGTH: 32 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:11:

```
        Phe  Pro  Asn  Trp  Tyr  Ile  Ser  Thr  Ser  Gln  Ala  Glu  Asn  Met  Pro  Val
        1              5                        10                            15

Phe  Leu  Gly  Gly  Thr  Lys  Gly  Gly  Gln  Asp  Ile  Thr  Asp  Phe  Thr  Met
                        20                        25                        30
```

( 2 ) INFORMATION FOR SEQ ID NO:12:

( i ) SEQUENCE CHARACTERISTICS:
        ( A ) LENGTH: 9 amino acids ( B ) TYPE: amino acid
( D ) TOPOLOGY: unknown ( i i ) MOLECULE TYPE: peptide ( x i ) SEQUENCE DESCRIPTION: SEQ ID NO:12:

```
Val Gln Gly Glu Glu Ser Asn Asp Lys
1               5
```

( 2 ) INFORMATION FOR SEQ ID NO:13:

( i ) SEQUENCE CHARACTERISTICS:
  ( A ) LENGTH: 50 amino acids
  ( B ) TYPE: amino acid
  ( D ) TOPOLOGY: unknown ( i i ) MOLECULE TYPE: peptide ( x i ) SEQUENCE DESCRIPTION: SEQ ID NO:13:

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Arg Lys Leu Thr Arg Met Leu Thr Phe Lys Phe Tyr Met Pro
            35                  40                  45
Lys Lys
    50
```

( 2 ) INFORMATION FOR SEQ ID NO:14:

( i ) SEQUENCE CHARACTERISTICS:
  ( A ) LENGTH: 50 amino acids
  ( B ) TYPE: amino acid
  ( D ) TOPOLOGY: unknown ( i i ) MOLECULE TYPE: peptide ( x i ) SEQUENCE DESCRIPTION: SEQ ID NO:14:

```
Glu Thr Cys Asn Lys Ser Asn Met Cys Glu Ser Ser Lys Ala Glu Leu
1               5                   10                  15
Ala Glu Asn Asn Leu Asn Leu Pro Lys Met Ala Glu Lys Asp Gly Cys
                20                  25                  30
Phe Gln Ser Gly Phe Asn Glu Glu Thr Cys Leu Val Lys Ile Ile Thr
            35                  40                  45
Gly Leu
    50
```

( 2 ) INFORMATION FOR SEQ ID NO:15:

( i ) SEQUENCE CHARACTERISTICS:
  ( A ) LENGTH: 35 amino acids
  ( B ) TYPE: amino acid
  ( D ) TOPOLOGY: unknown ( i i ) MOLECULE TYPE: peptide ( x i ) SEQUENCE DESCRIPTION: SEQ ID NO:15:

```
His Cys Pro Pro Thr Pro Glu Thr Ser Cys Ala Thr Gln Thr Ile Thr
1               5                   10                  15
Phe Glu Ser Phe Lys Glu Asn Leu Lys Asp Phe Leu Leu Val Ile Pro
                20                  25                  30
Phe Asp Cys
        35
```

( 2 ) INFORMATION FOR SEQ ID NO:16:

```
        ( i ) SEQUENCE CHARACTERISTICS:
                ( A ) LENGTH: 11 amino acids
                ( B ) TYPE: amino acid
                ( D ) TOPOLOGY: unknown ( i i ) MOLECULE TYPE: peptide ( x i ) SEQUENCE DESCRIPTION: SEQ ID NO:16:

Gln  Leu  Gln  Leu  Ser  Ala  Glu  Ser  Val  Gly  Glu
    1                   5                        10
```

( 2 ) INFORMATION FOR SEQ ID NO:17:

```
        ( i ) SEQUENCE CHARACTERISTICS:
                ( A ) LENGTH: 11 amino acids
                ( B ) TYPE: amino acid
                ( D ) TOPOLOGY: unknown ( i i ) MOLECULE TYPE: peptide ( i x ) FEATURE:
                ( A ) NAME/KEY: Modified-site
                ( B ) LOCATION: 11
                ( D ) OTHER INFORMATION: /note="The carboxy terminus may
                        be
                        amidated."

( x i ) SEQUENCE DESCRIPTION: SEQ ID NO:17:

Ser  Tyr  Gly  Arg  Gly  Asp  Val  Arg  Gly  Asp  Phe
    1                   5                        10
```

( 2 ) INFORMATION FOR SEQ ID NO:18:

```
        ( i ) SEQUENCE CHARACTERISTICS:
                ( A ) LENGTH: 10 amino acids
                ( B ) TYPE: amino acid
                ( D ) TOPOLOGY: unknown ( i i ) MOLECULE TYPE: peptide ( x i ) SEQUENCE DESCRIPTION: SEQ ID NO:18:

Ser  Gly  Ala  Tyr  Gly  Ser  Arg  Gly  Asp  Gly
    1                   5                        10
```

( 2 ) INFORMATION FOR SEQ ID NO:19:

```
        ( i ) SEQUENCE CHARACTERISTICS:
                ( A ) LENGTH: 18 amino acids
                ( B ) TYPE: amino acid
                ( D ) TOPOLOGY: unknown ( i i ) MOLECULE TYPE: peptide ( x i ) SEQUENCE DESCRIPTION: SEQ ID NO:19:

Pro  Ser  Tyr  Tyr  Arg  Gly  Asp  Gly  Ala  Pro  Ser  Tyr  Tyr  Arg  Gly  Asp
    1                   5                        10                       15

Gly  Ala
```

( 2 ) INFORMATION FOR SEQ ID NO:20:

```
        ( i ) SEQUENCE CHARACTERISTICS:
                ( A ) LENGTH: 25 amino acids
                ( B ) TYPE: amino acid
                ( D ) TOPOLOGY: unknown ( i i ) MOLECULE TYPE: peptide ( x i ) SEQUENCE DESCRIPTION: SEQ ID NO:20:

Pro  Ser  Tyr  Tyr  Arg  Gly  Asp  Gly  Ala  Pro  Ser  Tyr  Tyr  Arg  Gly  Asp
    1                   5                        10                       15

Ala  Pro  Ser  Tyr  Tyr  Arg  Gly  Asp  Ala
```

( 2 ) INFORMATION FOR SEQ ID NO:21:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:21:

Ala Arg Arg Ser Pro Ser Tyr Tyr Arg Gly Asp Ala Gly Pro Tyr Tyr
1               5                   10                  15

Ala Met Asp Tyr
            20

( 2 ) INFORMATION FOR SEQ ID NO:22:

( i ) SEQUENCE CHARACTERISTICS:
        ( A ) LENGTH: 9 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:22:

Tyr Arg Ala Leu Val Asp Thr Leu Lys
1               5

( 2 ) INFORMATION FOR SEQ ID NO:23:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:23:

Arg Ala Leu Val Asp Thr Leu Lys
1               5

( 2 ) INFORMATION FOR SEQ ID NO:24:

( i ) SEQUENCE CHARACTERISTICS:
        ( A ) LENGTH: 17 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:24:

Arg Ala Leu Val Asp Thr Leu Lys Phe Val Thr Gln Ala Glu Gly Ala
1               5                   10                  15

Lys ( 2 ) INFORMATION FOR SEQ ID NO:25:

( i ) SEQUENCE CHARACTERISTICS:
        ( A ) LENGTH: 16 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:25:

Tyr Ala Lys Phe Arg Glu Thr Leu Glu Asp Thr Arg Asp Arg Met Tyr
1               5                   10                  15

( 2 ) INFORMATION FOR SEQ ID NO:26:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:26:

```
Ala Lys Phe Arg Glu Thr Leu Glu Asp Thr Arg Asp Arg Met Tyr
1               5                   10                  15
```

( 2 ) INFORMATION FOR SEQ ID NO:27:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:27:

```
Tyr Ala Ala Leu Asp Leu Asn Ala Val Ala Asn Lys Ile Ala Asp Phe
1               5                   10                  15

Glu Leu
```

( 2 ) INFORMATION FOR SEQ ID NO:28:

( i ) SEQUENCE CHARACTERISTICS:
        ( A ) LENGTH: 17 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:28:

```
Ala Ala Leu Asp Leu Asn Ala Val Ala Asn Lys Ile Ala Asp Phe Glu
1               5                   10                  15

Leu
```

( 2 ) INFORMATION FOR SEQ ID NO:29:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:29:

```
Tyr Arg Ala Leu Val Asp Thr Leu Lys Phe Val Thr Glu Gln Ala Lys
1               5                   10                  15

Gly Ala
```

( 2 ) INFORMATION FOR SEQ ID NO:30:

( i ) SEQUENCE CHARACTERISTICS:
        ( A ) LENGTH: 17 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:30:

```
Arg Ala Leu Val Asp Thr Leu Lys Phe Val Thr Glu Gln Ala Lys Gly
1               5                   10                  15

Ala
```

( 2 ) INFORMATION FOR SEQ ID NO:31:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:31:

```
Tyr  Arg  Ala  Leu  Val  Asp  Thr  Glu  Phe  Lys  Val  Lys  Gln  Glu  Ala  Gly
 1                  5                        10                       15
Ala  Lys
```

( 2 ) INFORMATION FOR SEQ ID NO:32:

( i ) SEQUENCE CHARACTERISTICS:
        ( A ) LENGTH: 17 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:32:

```
Arg  Ala  Leu  Val  Asp  Thr  Glu  Phe  Lys  Val  Lys  Gln  Glu  Ala  Gly  Ala
 1                  5                        10                       15
Lys
```

( 2 ) INFORMATION FOR SEQ ID NO:33:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:33:

```
Tyr  Arg  Ala  Leu  Val  Asp  Thr  Leu  Lys  Phe  Val  Thr  Gln  Ala  Glu  Gly
 1                  5                        10                       15
Ala  Lys
```

( 2 ) INFORMATION FOR SEQ ID NO:34:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:34:

```
Val  Gly  Val  Ala  Pro  Gly  Val  Gly  Val  Ala  Pro  Gly  Val  Gly  Val  Ala
 1                  5                        10                       15
Pro  Gly
```

( 2 ) INFORMATION FOR SEQ ID NO:35:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:35:

```
Val  Pro  Gly  Val  Gly  Val  Pro  Gly  Val  Gly  Val  Pro  Gly  Val  Gly  Val
```

```
        1               5               10              15
```

Pro Gly Val Gly
             20

( 2 ) INFORMATION FOR SEQ ID NO:36:

( i ) SEQUENCE CHARACTERISTICS:
        ( A ) LENGTH: 6 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /note="Position 1 is a formylated Norleucine."

( i x ) FEATURE:
        ( A ) NAME/KEY: Modified-site
        ( B ) LOCATION: 4
        ( D ) OTHER INFORMATION: /note="Position 4 is a Norleucine."

( x i ) SEQUENCE DESCRIPTION: SEQ ID NO:36:

Xaa Leu Phe Xaa Tyr Lys
1               5

( 2 ) INFORMATION FOR SEQ ID NO:37:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /note="The N-terminus is formylated."

( x i ) SEQUENCE DESCRIPTION: SEQ ID NO:37:

Met Ile Phe Leu
1

( 2 ) INFORMATION FOR SEQ ID NO:38:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /note="The N-terminus is formylated."

( x i ) SEQUENCE DESCRIPTION: SEQ ID NO:38:

Met Leu Phe Lys
1

( 2 ) INFORMATION FOR SEQ ID NO:39:

( i ) SEQUENCE CHARACTERISTICS:
        ( A ) LENGTH: 4 amino acids
        ( B ) TYPE: amino acid
        ( D ) TOPOLOGY: unknown (ii) MOLECULE TYPE: peptide (ix) FEATURE:
 (A) NAME/KEY: Modified-site
 (B) LOCATION: 1
 (D) OTHER INFORMATION: /note="The N-terminus is formylated."

(xi) SEQUENCE DESCRIPTION: SEQ ID NO:39:

Met Leu Phe Ile
1

(2) INFORMATION FOR SEQ ID NO:40:

(i) SEQUENCE CHARACTERISTICS:
  (A) LENGTH: 4 amino acids
  (B) TYPE: amino acid
  (D) TOPOLOGY: unknown (ii) MOLECULE TYPE: peptide (ix) FEATURE:
  (A) NAME/KEY: Modified-site
  (B) LOCATION: 1
  (D) OTHER INFORMATION: /note="The N-terminus is formylated."

(xi) SEQUENCE DESCRIPTION: SEQ ID NO:40:

Met Phe Ile Leu
1

(2) INFORMATION FOR SEQ ID NO:41:

(i) SEQUENCE CHARACTERISTICS:
  (A) LENGTH: 4 amino acids
  (B) TYPE: amino acid
  (D) TOPOLOGY: unknown (ii) MOLECULE TYPE: peptide (ix) FEATURE:
  (A) NAME/KEY: Modified-site
  (B) LOCATION: 1
  (D) OTHER INFORMATION: /note="The N-terminus is formylated."

(xi) SEQUENCE DESCRIPTION: SEQ ID NO:41:

Met Phe Leu Ile
1

(2) INFORMATION FOR SEQ ID NO:42:

(i) SEQUENCE CHARACTERISTICS:
  (A) LENGTH: 4 amino acids
  (B) TYPE: amino acid
  (D) TOPOLOGY: unknown (ii) MOLECULE TYPE: peptide (ix) FEATURE:
  (A) NAME/KEY: Modified-site
  (B) LOCATION: 1
  (D) OTHER INFORMATION: /note="The N-terminus is formylated."

(xi) SEQUENCE DESCRIPTION: SEQ ID NO:42:

Met Leu Ile Phe
1

(2) INFORMATION FOR SEQ ID NO:43:

(i) SEQUENCE CHARACTERISTICS:
  (A) LENGTH: 4 amino acids
  (B) TYPE: amino acid (D) TOPOLOGY: unknown (ii) MOLECULE TYPE: peptide (ix) FEATURE:
    (A) NAME/KEY: Modified-site
    (B) LOCATION: 1
    (D) OTHER INFORMATION: /note="The N-terminus is formylated."

(xi) SEQUENCE DESCRIPTION: SEQ ID NO:43:

Met Ile Leu Phe
1

(2) INFORMATION FOR SEQ ID NO:44:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (xi) SEQUENCE DESCRIPTION: SEQ ID NO:44:

Thr Lys Pro Arg
1

(2) INFORMATION FOR SEQ ID NO:45:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (xi) SEQUENCE DESCRIPTION: SEQ ID NO:45:

Val Gly Val Ala Pro Gly
1               5

(2) INFORMATION FOR SEQ ID NO:46:

(i) SEQUENCE CHARACTERISTICS:
        (A) LENGTH: 5 amino acids
        (B) TYPE: amino acid
        (D) TOPOLOGY: unknown (ii) MOLECULE TYPE: peptide (xi) SEQUENCE DESCRIPTION: SEQ ID NO:46:

Tyr Ile Gly Ser Arg
1               5

(2) INFORMATION FOR SEQ ID NO:47:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note="The N-terminus is acetylated."

(xi) SEQUENCE DESCRIPTION: SEQ ID NO:47:

Tyr Ile Gly Ser Arg Cys
1               5

(2) INFORMATION FOR SEQ ID NO:48:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:48:

```
Asn Asp Gly Asp Phe Glu Glu Ile Pro Glu Glu Tyr Leu Gln
1               5                   10
```

(2) INFORMATION FOR SEQ ID NO:49:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 12
        (D) OTHER INFORMATION: /note="Position 12 is sulphonated (SO3Na)."

(xi) SEQUENCE DESCRIPTION: SEQ ID NO:49:

```
Asn Asp Gly Asp Phe Glu Glu Ile Pro Glu Glu Tyr Leu Gln
1               5                   10
```

(2) INFORMATION FOR SEQ ID NO:50:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (xi) SEQUENCE DESCRIPTION: SEQ ID NO:50:

```
Gly Pro Arg Gly
1
```

(2) INFORMATION FOR SEQ ID NO:51:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note="Position 1 is D-Phe."

(xi) SEQUENCE DESCRIPTION: SEQ ID NO:51:

```
Xaa Pro Arg Pro Gly Gly Gly Gly Asn Gly Asp Phe Glu Glu Ile Pro
1               5                   10                  15
Glu Glu Tyr Leu
            20
```

(2) INFORMATION FOR SEQ ID NO:52:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide ( x i ) SEQUENCE DESCRIPTION: SEQ ID NO:52:

Arg Arg Arg Arg Arg Arg Arg Arg Arg Gly Asp Val
1               5                   10

( 2 ) INFORMATION FOR SEQ ID NO:53:

( i ) SEQUENCE CHARACTERISTICS:
        ( A ) LENGTH: 13 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:53:

Pro Leu Tyr Lys Lys Ile Ile Lys Lys Leu Leu Glu Ser
1               5                   10

( 2 ) INFORMATION FOR SEQ ID NO:54:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:54:

Arg Gly Asp Ser
1

( 2 ) INFORMATION FOR SEQ ID NO:55:

( i ) SEQUENCE CHARACTERISTICS:
        ( A ) LENGTH: 12 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:55:

Glu Lys Pro Leu Gln Asn Phe Thr Leu Ser Phe Arg
1               5                   10

( 2 ) INFORMATION FOR SEQ ID NO:56:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 10
        ( D ) OTHER INFORMATION: /note="The C-terminus may be
            amidated (compound 1)."

( i x ) FEATURE:
        ( A ) NAME/KEY: Modified-site
        ( B ) LOCATION: 1
        ( D ) OTHER INFORMATION: /note="The N-terminus may be
            modified with 3,5-diisothiocyanato-benzoic acid
            ( c o m p o u n d   4 )."

( i x ) FEATURE:
        ( A ) NAME/KEY: Modified-site
        ( B ) LOCATION: 1
        ( D ) OTHER INFORMATION: /note="Two equivalents of the
            sequence may be modified at each of their
            N-termini with one equivalent of
            3,5- diisothiocyanato-benzoic acid to form a dimer
            ( c o m p o u n d   3 ).

(ix) FEATURE:
    (A) NAME/KEY: Modified-site
    (B) LOCATION: 1
    (D) OTHER INFORMATION: /note="The N-terminus may be modified with an acetyl group."

(ix) FEATURE:
    (A) NAME/KEY: Modified-site
    (B) LOCATION: 10
    (D) OTHER INFORMATION: /note="The C-terminus may be modified with hydrazine (compound 5)."

(ix) FEATURE:
    (A) NAME/KEY: Modified-site
    (B) LOCATION: 10
    (D) OTHER INFORMATION: /note="Two equivalents of the N-acetyl, C- hydrazine modified sequence may be further modified at the hydrazide with one equivalent of 3,5- diisothiocyanato-benzoic acid to form a dimer (compound 6)."

(ix) FEATURE:
    (A) NAME/KEY: Modified-site
    (B) LOCATION: 1
    (D) OTHER INFORMATION: /note="The N-terminus may be modified with Fmoc (compound 10)."

(ix) FEATURE:
    (A) NAME/KEY: Modified-site
    (B) LOCATION: 10
    (D) OTHER INFORMATION: /note="The N-Fmoc, C-hydrazine modified sequence may be further modified at the hydrazide with 3,5- diisothiocyanatobenzoic acid (compound 11)."

(ix) FEATURE:
    (A) NAME/KEY: Modified-site
    (B) LOCATION: 1..10
    (D) OTHER INFORMATION: /note="The N-hydrazide may be linked with the C- terminus through modification of both ends with 3,5- diisothiocyanatobenzoic acid (compound 12)."

(xi) SEQUENCE DESCRIPTION: SEQ ID NO:56:

```
Gly Asn His Trp Ala Val Gly His Leu Met
1               5                   10
```

METAL-BINDING TARGETED POLYPEPTIDE CONSTRUCTS

FIELD OF THE INVENTION

This invention relates to the preparation and use of novel targeted polypeptide constructs in which one or more polypeptide chains are chemically derivatized such that the resulting construct exhibits both metal-binding capability and tissue-, organ- or cell-targeting selectivity. In particular, the polypeptide constructs of the present invention comprise one or more polypeptide chains chemically derivatized to include two or more metal-binding groups selected from thioureas, thiosemicarbazides, acylthiosemicarbazides and combinations thereof. Neither the targeting polypeptide nor the chemical groups used to derivatize the targeting polypeptide alone can bind metal. Surprisingly, however, it has been discovered that the combination giving rise to the present invention provides both metal-binding and receptor-targeting characteristics in an integral compound. The metal complexes of the instant polypeptide constructs are useful in a wide variety of applications, including radiodiagnostic and radiotherapeutic treatment regimens. Metal complexes of lead-212, rhenium-186, and technetium-99m are particularly contemplated.

BACKGROUND OF THE INVENTION

It is known that certain peptides can be used as highly specific vehicles for the delivery of radioisotopes to target organs, tumors or thrombi in vivo. For example, somatostatin receptor-positive human tumors can be detected using radioiodinated analogues of somatostatin (Lamberts, S. W. J. et al., *N. Eng. J. Med.* (1990) 323:1246–1249; Krenning E. P. et al., *Lancet* (1989) 242–245; Bakker W. H. et al., *J. Nucl. Med.* (1990) 32:1501–1509). Rodwell et al., U.S. Pat. No. 5,196,510, showed that a radiolabeled peptide containing the amino acid sequence, RGD, could localize to thrombi in vivo, whereby thrombi could be scintigraphically imaged.

In nuclear medicine, the radiometal technetium-99m (Tc-99m) is a preferred isotope for scintigraphic imaging applications (Pinkerton et al., *J. Chem. Educ.* (1985) 62:965). Technetium is one of a class of metals ions which forms strong coordination bonds with sulfur-containing compounds, particularly thiols (e.g., metallothionein), but also with thioureas (Kopunec et al., *Radiochem. Radioanal. Lett.* (1977) 29:171).

Methods for the direct labeling of peptides with technetium have been reported which require the partial reduction of protein disulfide linkages to generate the free thiol groups that are capable of binding radiometals, specifically Tc-99m. Dean, U.S. Pat. No. 5,225,180, describes derivatives of somatostatin which contain at least 2 cysteine residues. The cysteine residues typically form a disulfide bond which, on reduction, form two sulfhydryl groups that are capable of coordinating to Tc-99m. Similarly, cysteine-containing amino acid sequences, which are derived from metallothionein, bind metals through these sulfhydryl moieties and can be incorporated into the amino acid sequence of targeting peptides to make radiopharmaceuticals (Rodwell, supra; Shoemaker, International Patent Publication No. WO90/06323). Alternatively, metallothionein or fragments thereof can be used to label proteins indirectly by conjugating them to biologically active molecules as described by Tolman, U.S. Pat. No. 4,732,864.

Direct radiolabeling methods, while advantageous, may not be possible or desirable in some cases. Many peptides, especially small ones, do not contain disulfide moieties and, therefore, cannot be labeled via direct methods without further chemical or recombinant modification of the peptide or protein to include disulfide bonds. Moreover, the reduction, itself, of the disulfide bonds can denature, fragment or aggregate the peptide or cause deviations from native conformations that may compromise peptide-receptor binding and, otherwise, compromise the biological targeting capability of the radiolabeled product. If the targeting protein contains more than one disulfide, the current methods provide no way of distinguishing between the disulfides and, hence, no means for directing the metal to a particular metal-binding site.

It has further been shown that targeting proteins can also be radiolabeled by covalently linking or conjugating chelating ligands capable of binding metals to the targeting proteins. Albert et al., International Patent Publication No. WO91/01144, disclose biologically active peptides bearing at least one chelating ligand linked to an amino group of the peptide useful as a radiopharmaceutical for in vivo imaging of target tissues or for therapy. The chelating ligand must be linked to an amino group that is not involved in the binding of the peptide to the targeted receptor. The chelating ligands disclosed include polyamine or imine carboxylic acid chelators, e.g., EDTA, DTPA, etc.; C-functionalized tetraazacyclododecanetetraacetic acids; N-substituted or C-substituted macrocyclic amines; bis-aminothiol alkylene derivatives; ethylene dithiosemicarbazone derivatives; ligands derived from propylene amine oxime derivatives; and ligands derived from diamide dimercaptides. Fritzberg, European Patent No. 0 188 256 A2, describes N,N'-bismercaptoacetyl-w,(w-x)-diamino carboxylic acid esters conjugated to polypeptides.

Yokoyama et al., U.S. Pat. No. 4,287,362; *Int. J. Nucl. Med. Biol.* (1986) 12:425; *J. Nucl. Med.* (1987) 28:1027, describe bifunctional chelators similar to Albert et al., supra, based on N-methylthiosemicarbazone derivatives of 1,2-dicarbonyl compounds. These bifunctional compounds have two N-methylthiosemicarbazone binding groups on one side of the chelating ligand while the opposite side contains a functional group to which the targeting protein is covalently attached. Analogous systems are described by Wu, EP 0306168, which are also based on thiosemicarbazone derivatives of dicarbonyl compounds. Arano et al., *Int. J. Nucl. Med. Biol.* (1986) 12(6):425–430, teach the use of a chelating agent, p-carboxyethyl-phenylglyoxal-di(N-methylthiosemicarbazone), to radiolabel biologically interesting molecules.

Troutner, U.S. Pat. No. 5,101,041, describes functionalized triamine chelating ligands that are covalently attached to proteins. McBride et al., U.S. Pat. No. 5,080,884, disclose hydrocarbylphenyl diaminodithiol radionuclide complexes. No biological targeting moieties are disclosed.

Thus, previous work has relied on the covalent attachment of a chelating ligand to a biological targeting moiety, like a protein, to provide a targettable radiolabel. Unfortunately, chemistries for conjugating chelators to targeting peptides are often not compatible with the biological targeting moiety. Hence, the biological activity of the targeting peptides or proteins is not always preserved. Additionally, free thiols are somewhat unstable to oxidation/dimerization and may, in turn, reduce disulfide bonds or react with a free sulfhydryl group elsewhere in the same peptide or in neighboring peptides. Free cysteines may recombine to disulfide groups through air oxidation, eliminating metal coordinating thiol groups. The thiol functions in typical chelators that can be attached to peptides must be protected during final steps of synthesis and then deprotected just before technetium binding. These steps are somewhat cumbersome for radiolabeling. Such chemistries can also be difficult or exceedingly tedious, adding numerous steps (including additional purification procedures) and expense to the overall synthesis of the targeting-chelator compounds. Furthermore, such manipulations can unduly complicate the radiolabeling procedure. Moreover, the covalent linkage provided by current conjugation chemistries is not always stable. For example, thiosemicarbazone derivatives or imine derivatives, which are formed by a condensation reaction that results in the removal of water, may be subsequently susceptible to undesired hydrolysis. Such compounds can be expected to hydrolyze easily in an acidic environment or in vivo prematurely, leading to the disintegration of the targeting protein metal-chelate conjugate.

Hence, there remains a need for a simple targettable construct that possesses strong label-binding characteristics and in vivo or in vitro targeting specificity. A desirable targettable construct would be one that is easily made, with a minimum number of synthetic steps, yet retain the versatility to accommodate a number of types of labels and starting biological targeting species, particularly proteins and peptides. Such a desirable targettable construct would even be directable to more than one type of receptor at any given time. In addition, such a desirable targettable label would be amenable to the on-site radiolabeling procedure that is typical of short half-life radiopharmaceutical products. While being especially useful in in vivo or in vitro diagnostic applications, such a targettable construct would also find application in the therapeutics arena.

SUMMARY OF THE INVENTION

It is therefore an object of the present invention to provide a novel class of targettable construct label that fulfills the needs stated above. It is further an object of the present invention to provide chemistries that are compatible with a variety of biological molecules, including proteins and peptides, and which preserve the selective targeting function of the biological molecule. It is yet another object of the invention to provide targettable constructs, which are directable to one or more sites in the body, organ, tissue or cell, as the case may be, by providing homo- (the same polypeptide chain) or hetero- (different polypeptide chains) multivalent targeting moieties. Moreover, such multivalent targettable constructs can afford greater diagnostic sensitivity in targeting an organ, tissue or cell that expresses more than one type of receptor target. It is also an object of the invention to provide stable metal-binding integral polypeptide constructs in which the overall size of the resulting targettable construct is dictated primarily by the molecular size of the starting biological targeting species and not the metal-binding region of the targettable construct.

Thus, according to the present invention, a metal-binding targeted polypeptide construct is provided which comprises a compound of the formula (I):

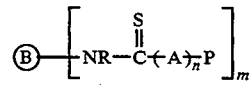

(I)

in which,

"B" is a saturated or unsaturated aliphatic or aromatic hydrocarbon backbone comprising 1–20 carbon atoms and, optionally, one or more heteroatoms selected from the group consisting of nitrogen, oxygen, phosphorus and sulfur; "P" is a polypeptide comprising 2–100 amino acids, the polypeptide capable of targeting particular cells, tissues or organs of the body;

"A" may be the group —NR'—NR"— or the group —NR'—NR"—L— in which L may be an aliphatic or aromatic linker group comprising 1–12 carbon atoms and, optionally, one or more heteroatoms selected from the group consisting of nitrogen, oxygen, phosphorus and sulfur;

R, R', and R" may be the same or different and may be hydrogen or an aliphatic group comprising 1–6 carbon atoms and, optionally, one or more heteroatoms selected from the group consisting of nitrogen, oxygen, phosphorus and sulfur;

m is an integer $\geq 2$, provided that the groups R, R', R", L and "P" of a given chain may be the same or different from the groups R, R', R", L and "P" of another chain;

n is an integer $\geq 0$, $\leq 2$;

or a pharmaceutically acceptable salt thereof.

In the present invention, whenever a hydrocarbon group further optionally comprises one or more heteroatoms, such heteroatom or heteroatoms may be present either in the hydrocarbon chain or as part of functional groups attached to the hydrocarbon chain.

The present invention also contemplates metal complexes of the formula (II):

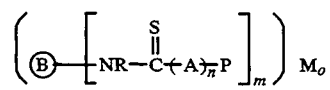

(II)

in which,

"B" is a saturated or unsaturated aliphatic or aromatic hydrocarbon backbone comprising 1–20 carbon atoms and, optionally, one or more heteroatoms selected from the group consisting of nitrogen, oxygen, phosphorus and sulfur; "P" is a polypeptide comprising 2–100 amino acids, the polypeptide capable of targeting particular cells, tissues or organs of the body;

"A" may be the group —NR'—NR"— or the group —NR'—NR"—L— in which L may be an aliphatic or aromatic linker group comprising 1–12 carbon atoms and, optionally, one or more heteroatoms selected from the group consisting of nitrogen, oxygen, phosphorus and sulfur;

R, R', and R" may be the same or different and may be hydrogen or an aliphatic group comprising 1–6 carbon atoms and, optionally, one or more heteroatoms selected from the group consisting of nitrogen, oxygen, phosphorus and sulfur;

m is an integer $\geq 2$, preferably 2–4, most preferably 2, provided that the groups R, R', R", L and "P" of a given chain may be the same or different from the groups R, R', R", L and "P" of another chain;

n is an integer ≧0, ≦2;

o is an integer ≧1, ≦m;

"M" is a metallic moiety;

or a pharmaceutically acceptable salt thereof.

In particular, the metallic moiety comprises a metal selected from the group consisting of transition metal elements, lanthanide metal elements, and actinide metal elements and is preferably a radioisotope.

It is also an object of the present invention to provide pharmaceutical compositions comprising the compound of formula (I) or the complex of formula (II) or combinations of both and a pharmaceutically acceptable carrier.

It is likewise an object of the present invention to provide new methods of obtaining an image of an internal region of a subject comprising administering to a subject an effective amount of the complex of formula (II) in which the metallic moiety comprises a radioisotope, and recording the scintigraphic image obtained from the decay of the radioisotope. Other objects of the present invention include methods of enhancing an MR image of an internal region of a subject comprising administering to a subject an effective amount of the complex of formula (II) in which the metallic moiety comprises a paramagnetic metal, and recording the MR image of an internal region of the subject; a method of enhancing a sonographic image of an internal region of a subject comprising administering to a subject an effective amount of the complex of formula (II), and recording the sonographic image of an internal region of the subject; and a method of enhancing an X-ray image of an internal region of a subject comprising administering to a subject an effective amount of the complex of formula (II), and recording the X-ray image of an internal region of the subject.

The present invention also discloses compounds useful, for example, as intermediates in the synthesis of the compounds of the formula (I). Such intermediate compounds include those of the formula (III):

in which,

"B" is a saturated or unsaturated aliphatic or aromatic hydrocarbon backbone comprising 1-20 carbon atoms and, optionally, one or more heteroatoms selected from the group consisting of nitrogen, oxygen, phosphorus and sulfur;

"P" is a polypeptide comprising 2-100 amino acids, the polypeptide capable of targeting particular cells, tissues or organs of the body;

"A" may be the group —NR'—NR"— or the group —NR'—NR"—L— in which L may be an aliphatic or aromatic linker group comprising 1-12 carbon atoms and, optionally, one or more heteroatoms selected from the group consisting of nitrogen, oxygen, phosphorus and sulfur;

R, R', and R" may be the same or different and may be hydrogen or an aliphatic group comprising 1-6 carbon atoms and, optionally, one or more heteroatoms selected from the group consisting of nitrogen, oxygen, phosphorus and sulfur;

m is an integer ≧1, provided that the groups R, R', R", L and "P" of a given chain may be the same or different from the groups R, R', R", L and "P" of another chain;

n is an integer ≧0, ≦2;

q is an integer ≧1;

or a pharmaceutically acceptable salt thereof.

Hence, a specific object of the present invention is the disclosure of a radiodiagnostic agent comprising a radionuclide and a compound of the formula (I), as described above and, in further detail, below. Pharmaceutical kits are also disclosed which comprise a predetermined amount of the compound of formula (I) and, optionally, a pharmaceutically acceptable carrier, stabilizer, preservative, or reducing agent.

Yet another object of the present invention is the disclosure of methods of treatment, including a method of treating a subject comprising administering to a subject an effective amount of the compound of formula (I) complexed to a transition, lanthanide or actinide metal. The metal may simply be a heavy metal that is toxic to the selected cells (e.g., platinum) or, preferably, the metal is a radiotherapeutic metal (e.g., rhenium-186).

Other objects of the present invention will become apparent to those of ordinary skill in the art, especially upon further consideration of the detailed description of the preferred embodiments presented below.

DETAILED DESCRIPTION OF THE PREFERRED EMBODIMENTS

Figure 1:
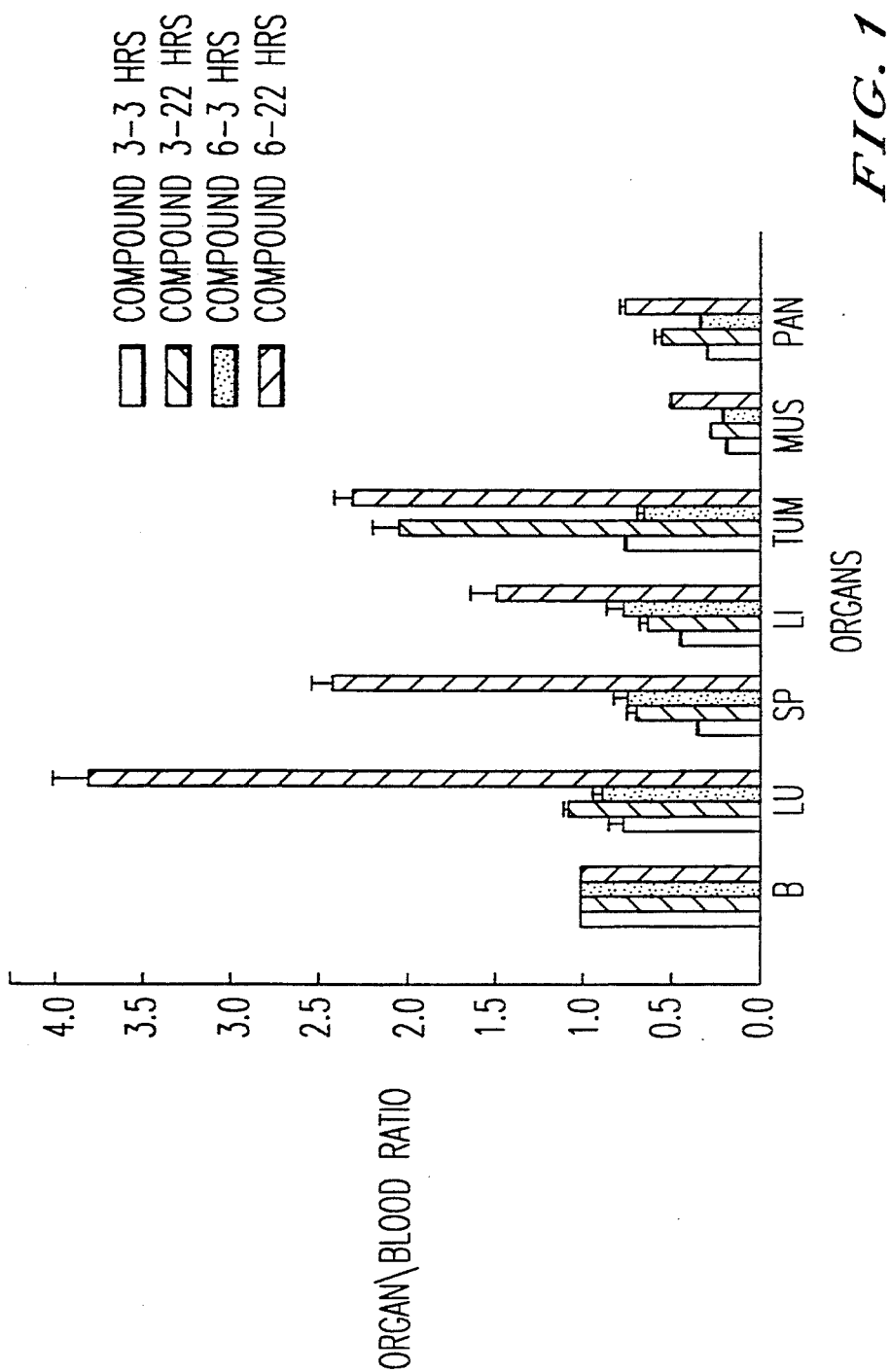
FIG. 1 presents the biodistribution in mice bearing HT-29 colon carcinoma xenograft tumors of two different Tc-99m-labeled bis-Neuromedin C compounds, 3 and 6. The data for each organ are reported as the counts per minute (CPM) or Tc-99m per gram of organ divided by the CPM per gram of blood (organ to blood ratio). The abbreviations for each organ are: B—blood; LU—lung; SP—spleen; LI—liver; RK—kidney; TUM—tumor; MUS—muscle; and PAN—pancreas. The results presented were obtained after 3 hr   compound 3;  , compound 6) and 22 hr (  , 3;  , 6), respectively. A tumor:blood ratio that approaches or exceeds unity and increases with time is indicative of targeted localization in the tumor. Compound 3 had a tumor:blood ratio of 0.71 at 3 hrs, increasing to 2.0 by 22 hrs. Compound 6 had a 0.62 tumor:blood ratio increasing to 2.25 by 22 hrs.

5.1 General Aspects of the Targeting Construct

The present invention relates to a metal-binding targeted polypeptide construct comprising a compound of the formula (I):

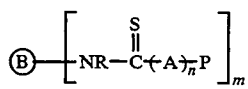

in which,

"B" is a saturated or unsaturated aliphatic or aromatic hydrocarbon backbone comprising 1-20 carbon atoms and, optionally, one or more heteroatoms selected from the group consisting of nitrogen, oxygen, phosphorus and sulfur;

"P" is a polypeptide capable of targeting particular cells, tissues or organs of the body; as used herein, the term "polypeptide" includes peptides, comprising as few as two amino acids, and medium-sized proteins, comprising up to about 100 amino acids or more in length;

"A" may be the group —NR'—NR"— or the group —NR'—NR"—L— in which L may be an aliphatic or aromatic linker group comprising 1-12 carbon atoms and, optionally, one or more heteroatoms selected from the group consisting of nitrogen, oxygen, phosphorus and sulfur;

R, R', and R" may be the same or different and may be hydrogen or an aliphatic group comprising 1-6 carbon atoms and, optionally, one or more heteroatoms selected from the group consisting of nitrogen, oxygen, phosphorus and sulfur;

m is an integer $\geq 2$, provided that the groups R, R', R", L and "P" of a given chain may be the same or different from the groups R, R', R", L and "P" of another chain;

n is an integer $\geq 0$, $\leq 2$;

or a pharmaceutically acceptable salt thereof.

The polypeptide moiety "P" may be attached covalently to the rest of the compound by any of the functional groups normally present in a peptide or protein, typically either through an amino group or a carboxylic acid group. In a particular, preferred embodiment of the present invention, the group "A" of the compound of formula (I) is —NR'—NR"— when "P" is attached to "A" by a carboxylic acid group of the polypeptide. In another embodiment of the invention, the group "A" is —NR'—NR"—L— when "P" is attached to "A" by an amino group of the polypeptide. In yet another specific embodiment, the group "P" is attached to the thiocarbonyl group of the formula (I) by an amino group of the polypeptide when n=0 (i.e., when there is no group "A" present in the compound).

As noted previously, the group "B" is a saturated or unsaturated, cyclic or acylic aliphatic or aromatic hydrocarbon backbone comprising 1-20 carbon atoms and, optionally, further comprising one or more heteroatoms selected from the group consisting of nitrogen, oxygen, phosphorus and sulfur. Hence, the hydrocarbon backbone may be a straight or branched aliphatic chain, such as $C_1-C_8$ alkylene chain, preferably $C_2-C_6$, and may have one or more substituents, including functional groups that can accommodate a charge (e.g., —CO$_2$H or —NR$_2$) or can allow the construct to be linked, preferably covalently, to a separate chemical entity. Examples of such substituents or functional groups include, but are not limited to, hydroxy, amino, halo, epoxy, formyl, carboxylic acid, ester, amide, carboxylic acid hydrazide, semicarbazide, thiosemicarbazide, isothiocyanate, and even one or more sites of unsaturation (i.e., a double or triple bond). Other examples include the presence of heteroatoms in the aliphatic chain, such as polyalkyleneamino, oxo, thio or phosphonic acid or ester chains. Polyamines and polyethers are preferable.

In one embodiment of the invention, the hydrocarbon backbone "B" is a 1-carboxy-1,5-pentylene chain. With this backbone, an intramolecular condensation reaction can take place in which the amino group, —NR'— where R' is an H, of the thiourea group alpha to the carboxylic acid group of the backbone, combines with the carboxylic acid with loss of water to form a thiohydantoin group, as illustrated in the Examples Section below.

Hence, in one embodiment of the present invention, at least one set of the groups R and R' forms a cyclic array with the thiourea group when n is not zero. In particular, this cyclic array can be a thiohydantoin group that is covalently linked to the hydrocarbon backbone "B".

As stated above, the hydrocarbon backbone "B" may also comprise an aromatic group. The aromatic group, for example, may be an aryl group having one or more aromatic rings (e.g., phenyl, naphthyl, and the like). As in the aliphatic chain described above, the aromatic group may further comprise a substituent or functional group that can accommodate a charge or allow linkage of the backbone to a separate chemical entity. A preferred aromatic backbone is a mono-, di-, or tri-substituted benzoic acid, ester, amide, hydrazide, or like analog thereof.

The group "A" may or may not be present in the compounds of the present invention. In a particular embodiment, then, the polypeptide "P" is attached directly to the thiocarbonyl group, preferably by an amino group of the polypeptide, to provide a thiourea group, which together with a second, third, or fourth thiourea, thiosemicarbazide or acylthiosemicarbazide group, allows the construct to bind metallic species. If the group "A" is present, it may either be the group —NR'—NR"— or the group —NR'—NR"—L— in which L may be an aliphatic or aromatic linker group comprising 1-12 carbon atoms and, optionally, one or more heteroatoms selected from the group consisting of nitrogen, oxygen, phosphorus and sulfur. Preferably, this linker group is an straight or branched aliphatic chain comprising 1-10 carbon atoms and may comprise the side chain of an amino acid residue, such as serine, threonine, lysine, arginine, histidine, aspartic acid, glutamic acid, hydroxyproline, asparagine, glutamine, cysteine, methionine, phenylalanine, tyrosine, tryptophan, and even non-naturally occurring amine acids.

As noted previously, the R, R', and R" groups may be the same or different and may be hydrogen or an aliphatic group comprising 1-6 carbon atoms. These "R" groups, optionally, may further comprise one or more heteroatoms selected from the group consisting of nitrogen, oxygen, phosphorus and sulfur.

Also, because the metal-binding targeted polypeptide construct of the present invention comprises two or more polypeptide chains, in the case of open-chain constructs, the groups R, R', R", L and "P" of a given chain may be the same or different from the groups R, R', R", L and "P" of another chain. Moreover, the group "P" of one chain may be linked covalently to a "P" of another chain (e.g., by disulfide bonds between two cysteine residues or amide bonds through side chains). Alternatively, the ends of the two polypeptide chains which are most distant from the metal-binding site of the construct (the "distal" ends) may be linked together to form a contiguous, cyclized polypeptide chain. Such a cyclic construct, then, may be properly considered to have one "P" group. Preferably, the "P" group of a cyclic construct will have a minimum of three to four amino acid residues. Overall, the group "P" may comprise 2–100 amino acid residues, preferably 3–50, most preferably 3–25.

As should be apparent from the present disclosure, the targeted polypeptide constructs of the invention comprise targeting peptides or proteins that have been chemically derivatized to include thiocarbonyl groups capable of coordinate binding with a metal. The thiocarbonyls are preferably thioureas, thiosemicarbazides, acyl- or thioacylsemicarbazides, and similar aminothiocarbonyl-containing analogs. The compounds of the present invention are preferably formed by reacting diamine or polyamine compounds, such as those that are 1,2-, 1,3-, 1,4-, 1,5-diamine substituted alphatic and aromatic compounds, with thiophosgene (or a thiophosgene equivalent) to form a di- or polyisothiocyanate. The diisothiocyanate product obtained from a diamino compound is susceptible to nucleophilic attack by a polypeptide or polypeptide derivatized by specific linker groups, such as the group —NR'—NR"—L—, discussed above, resulting in the formation of thiocarbonyl-containing groups derived from the diisothiocyanates.

The metal-binding targeted polypeptide constructs of the present invention are prepared from an isothiocyanate starting material, preferably a 1,2-, 1,3-, 1,4- or 1,5-diisothiocyanate, and more preferably a 1,2 or 1,3- diisothiocyanatobenzoic acid. The polyisothiocyanates are, in turn, obtained readily from polyamines, or reducible polynitro-substituted compounds.

In a specific embodiment of the present invention, it is contemplated that the isothiocyanate groups of the starting materials for the group "B" are substituents on an aliphatic hydrocarbon backbone chain, preferably of two or more carbons, e.g., ethylene, propylene, butylene, pentylene. In another embodiment, the backbone "B" may be an aromatic or aryl-containing hydrocarbon. As used herein, the term "aryl" refers to a conjugated system of pi electrons having $4n+2$ number of pi electrons (where $n =$ an integer $\geq 1$). Aryl groups include, but are not limited to, polysubstituted benzenes, pyridines, furans, pyroles and the like. In specific embodiments, infra, the backbone is a 1,2-substituted benzene ring or a 1,3-substituted benzene ring. For purposes of this discussion, the numerical positions of the various substituents reflect their positions on the backbone relative to each other.

Polyisothiocyanates, especially diisothiocyanates, can be prepared by well known methods in the art (e.g., D'Angeli et al., *J. Org. Chem.* (1963) 28:1596–1600; Lieber and Slutkin, *J. Org. Chem.* (1962) 27:2214–2217; and Klöpping and van der Kerk, *Rec. Trav. Chim.* (1951) 70:949–961). In a specific embodiment, diisothiocyanates can be prepared by reacting a diamine substituted backbone group or an analogous compound with excess thiophosgene, with the proviso that the diamines not be in close enough proximity or on a sufficiently flexible backbone such that an intramolecular cyclization reaction occurs. Such undesired cyclization can occur by nucleophilic attack of an unreacted amine on the neighboring isothiocyanate. Generally, preparation of diisothiocyanates are well known reactions. The specific reaction conditions will depend on the choice of diamine or diamine analog. Because the backbone may also have a functional group, care must be taken to protect that functional group if it could itself undergo chemical conversion or interact with the isothiocyanate functional groups being prepared in the reaction. For example, if such a functional group contains a free amine, the amine can be blocked with a protecting group such as tert-butoxycarbonyl group. The tert-butoxycarbonyl group can be removed subsequently by treatment with trifluoroacetic acid. For a listing of potentially useful protecting groups, the reader is referred to "Protective Groups in Organic Synthesis" 2nd Edition, T. W. Greene and P. G. M. Wuts, John Wiley & Sons, New York, N.Y., 1991.

In a specific embodiment, the backbone comprises a benzene ring. When a 1,2-disubstituted benzene ring is used, a preferred starting material for reaction with thiophosgene is benzimidazole (e.g., 5-benzimidazolecarboxylic acid). The nitrogens of the imidazole ring are reactive with thiophosgene. If free amines in the 1,2-positions, rather than the imidazole ring, were reacted with thiophosgene, a significant if not dominant side reaction of nucleophilic attack by one amine at the isothiocyanate derivative of the other amine would probably occur. Thus, to avoid this cyclization reaction, the benzimidazole group is used (See, Hull, Synthetic Commun. (1979) 9:477–481) to generate a 1,2-diisothiocyanate on the benzene ring.

In the situation in which a 1,3-disubstituted benzene ring is used, the free amines can be reacted with thiophosgene to give a 1,3-diisothiocyanatobenzene. Although the present invention is not limited to a particular mechanism, it is believed that the rigid structure of the benzene ring, which has little conformational freedom, and the distance between the amines in the 1,3-positions preclude reaction of one amine with the isothiocyanate derivative of the other amine, and allows both amines to react with thiophosgene.

In the situation in which lysine is used, the alpha and epsilon amines can be reacted with thiophosgene to form isothiocyanates. Upon substitution of the alphaisothiocyanate with peptide, a further intramolecular reaction may occur with nucleophilic attack at the carboxylic acid of lysine to form a thiohydantoin derivative, if a suitable leaving group is present (e.g., when the carboxylic acid is in the form of an ester).

The targeted constructs of the present invention are then produced by allowing the polypeptide of interest, in its underivatized, zwitterionic form (i.e., in its unprotected form) or in a partially protected form which focuses the reaction with the isothiocyanate to a particular nucleophilic or amino group locus (e.g., N-acetyl obtained by acetylating the amino terminus) or as a nucleophilic derivative thereof (e.g., a carboxylhydrazide obtained by allowing the carboxy terminus to react with hydrazine or an N-hydrazinoacyl compound obtained by allowing the amino terminus to react with hydrazine-substituted acylating agent) to undergo a reaction with the isothiocyanate substituents of the group "B."

The reaction of the nucleophile with the isothiocyanate substituents can be performed under fairly standard conditions. Generally, for example, the diisothiocyanate and the reactive nucleophile are combined in an inert polar aprotic solvent in which both compounds are soluble. Examples of such solvents are acetonitrile, dimethylformamide, or dioxane. On occasion, protic mixtures containing water, alcohols or the like may also be used. Generally, the reaction can be run at room temperature, although where a difficult nucleophilic addition to the isothiocyanate is contemplated, the temperature can be increased above room temperature. When the "P" groups have the same amino acid sequence, the polypeptide can be added at greater than a two-fold molar excess over the diisothiocyanate to ensure quantitative di-addition. Where two different polypeptides are contemplated, one can take advantage of the fact that the isothiocyanate groups may have differential reactivity (that is, that the addition reaction may occur rapidly to one isothiocyanate but more slowly to the second). Thus, by adding a limiting amount of the nucleophile, e.g., one molar equivalent of nucleophile for each mole of diisothiocyanate, reaction at a single isothiocyanate can be effected. Subsequently, one or more molar equivalents of a second nucleophile, e.g., a different peptide, can be added to the monosubstituted diisothiocyanate to yield a disubstituted polypeptide construct. In a specific example, infra, monosubstituted and disubstituted constructs are obtained.

5.2. Targeting Peptides and Proteins

Generally, any peptide or protein may be chemically derivatized according to the method of the present invention to include specifically at least one of the metal-binding groups of interest, namely, thiourea, thiosemicarbazide, acylthiosemicarbazide and the like. It should be pointed out, in addition, that the acyl group of the acylthiosemicarbazide can be a thioacyl, iminoacyl, alkylimino, and the like. However, the present invention focuses on those peptides and proteins (i.e., the "targeting" peptides or proteins) that have an affinity for particular receptors, preferably receptors that are expressed uniquely on the surface of a particular organ, tissue or cell. Broadly, general classes of potential targets, in addition to receptors, include, but are not limited to, antigens, nucleic acids, enzymes, and selected proteins. Particular examples, include, but are not limited to, receptors of gastrin releasing peptide receptor (GRPr), epidermal growth factor receptor (EGFr), platelet-derived growth factor receptor (PDGFr), tumor necrosis factor receptor (TNFr), fibroblast growth factor receptor (FGFr), insulin-like growth factor receptor (IGHr), transferrin receptor, laminin receptor, cytokine receptors, fibronectin receptor, interleukin receptors, interferon receptors, etc.; antigens that are recognized by complementarily determining regions of antibodies (CDR), carcinoembryonic antigen (CEA), TAG-72, mucin (MUC) antigens, CD antigens, prostate specific antigens (PSA), prostate alkaline phosphatase (PAP), prostate mucin antigens (PMA), recognized by the monoclonal antibody PD-41 (U.S. Pat. No. 5,227,471), the antigen recognized by the monoclonal antibody 7Ell-C5 (U.S. Pat. 5,162,504), transcription regulatory elements, urokinase, cathepsin D, cytoskeletal proteins, signal transduction proteins, ion channel related proteins, histones, nuclear membrane proteins oncogene products (i.e., p53), cadherins, and steroid hormone receptors.

Thus, in particular embodiments of the present invention, polypeptides such as, but not limited to, those listed below may be used advantageously in the contemplated constructs.

2-50 AMINO ACIDS:

Neuromedin C: GNHWAVGHLM (10 aa) (SEQ. ID NO: 1)

Neuromedin B: GNLWATGHFM (10 aa) (SEQ. ID NO: 2)

Gastrin: LEGPWLFEEEAYGWMDG (17 aa) (SEQ. ID NO: 3)

Laminin peptide: IKVAVS (6 aa) (SEQ. ID NO: 4) (Royce et al. 1992 Invasion Metastasis 12:149–55)

Laminin peptide: YIGSR (5 aa) (SEQ. ID NO: 5) (an example of a heterofunctinal might be IKVAVS and YIGSR)

Luteinizing Hormone-Releasing Hormone: EHWSYGLRPG (10 aa) (SEQ. ID No:6)

LHRH analog: EHWSY-dW-LRPG (see, Shally et al. in "Vitamins and Hormones" (1980) Munson et al. (Eds.) Academic Press, New York, pp. 257–323.

RGD (3 aa)

Somatostain: AGCKNFFWKTFTSC (14 aa) (SEQ. ID NO: 7), (FWKT critical sequence, or YWKT) (Bakker et al.)

IFG-1, Insulin like growth factor-1, B domain: GPETLCGAELVDAALQFVCGDRG-FYFNKPT (30 aa) (SEQ. ID NO: 8) or GPETLCGAELVDAALQFVCGDRGFYFNKPTGYG (33 aa) (SEQ. ID NO: 9) (Cascieri et al. 1988 Biochemistry 27:3229

Interleukins:

IL-1 β: residues 172–196: NDKIPVALGLKEKN-LYLSCVLKDD (24 aa) (SEQ. ID NO: 10) residues 237–298: FPNWYISTSQAENMPVFLGGTKGG-QDITDFTM (32 aa) (SEQ. ID NO: 11) (Palaszynski 1987 Biochem Biophys Res Commun 147:204–211) residues 163–171: VQGEESNDK (9 aa) (SEQ. ID NO: 12) (Boraschi et al. 1988 J Exp Med 168:675–686)

IL-2: amino terminal 50 aa: (SEQ. ID NO: 13) APTSSSTKKTQLQLEHLLLDLQMILNGIN-NYKNPRKLTRMLTFKFYMPKK (SEQ. ID NO: 13) (Altman et al. 1984 PNAS USA 81:2176–2180; Kuo and Robb 1986 J Immunol 137:1538–1543; Ju et al. 1987 J Biol Chem 262:5723–5731)

IL-6: residues 42–91: ETCNKSNMCESSKAELA-ENNLNLPKMAEKDGCFQSGFNEETCL-VKIITGL (50 aa) (SEQ. ID NO: 14) (Hirano and Kishimoto 1991 in Peptide Growth Factors and Their Receptors I, Sporn and Roberts (eds) Springer-Verlag, New York)

GM-CSF, Granulocyte-macrophage Colony Stimulating Factor β: residues 88–121:HCPPTPETSCATQ-TITFESFKENLKDFLLVIPFDC (36 aa) (SEQ. ID NO: 15) (Burgess 1991, in Peptide Growth Factors and Their Receptors I, Sporn and Robers (eds) Springer, Verlag, New York)

FGF b, Fibroblast Growth Factor: residues 105–115: QLQLSAESVGE (SEQ. ID NO: 16) (biard et al. 1988 PNAS USA 85:2324–2328; Schubert et al. 1987 J Cell Bio 104:635–643)

50–~100 AMINO ACIDS:

EGF, Epidermal Growth Factor: (53 aa)

TGF-β, Transforming growth factor β: (112 aa)

TGF-α, Transforming growth factor α: (50 aa)
IGF-I, Insulin like growth factor I: (70 aa)
IFG-II, Insulin like growth factor II: (67 aa)

While other targeting proteins may be larger, advanced research may reveal a portion of the protein, which is responsible for binding to the target, or a mimetic may be discovered which is also capable of binding to the target. Such other developments, including polypeptide analogs, should be considered to fall within the scope of the present invention.

The key to the three-letter and single-letter abbreviations used in this disclosure can be found in Table I, presented below. The single letter designations, when used in the instant disclosure, will appear in italicized form.

TABLE I

| Amino Acid Abbreviations | | |
|---|---|---|
| Amino acid | Three-letter symbol | One-letter symbol |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| serine | Ser | S |
| Threonine | Thr | T |
| Tryptophan | Trp | W |
| Tyrosine | Tyr | Y |
| Valine | Val | V |

For additional examples of specific amino acid sequences that would be of particular interest, the reader is referred to the disclosure of Rodwell et al., U.S. Pat. No. 5,196,510, the complete disclosure of which is incorporated herein by reference. A preferred polypeptide would be RGD, which would allow the construct to localize to thrombi in vivo. Other polypeptides of interest include SYGRGDVRGDF, SGAYGSRGDG, PSYYRGDGAPSYYRGDGA, PSYYRGDGAPSYYRGDAPSYYRGDA, and ARRSPSYYRGDAGPYYAMDY (SEQ. ID NOS: 17, 18, 19, 20, and 21, respectively).

Other peptides of interest include those disclosed by in International Application No. WO 92/13572, the complete disclosure of which is incorporated herein by reference. In particular, selected peptides include:

I. Atherosclerotic Plaque Binding Peptides

YRALVDTLK (SEQ. ID NO: 22)
RALVDTLK (SEQ. ID NO: 23)
RAL VDTLKFVTQ AE GAK (SEQ. ID NO: 24)
YAKFRETLEDTRDRMY (SEQ. ID NO: 25)
AKFRETLEDTRDRMY (SEQ. ID NO: 26)
YAALDLNAVANKIADFEL (SEQ. ID NO: 27)
AALDLNAVANKIADFEL (SEQ. ID NO: 28)
YRAL VDTLKFVTEQ AK GA (SEQ. ID NO: 29)
RAL VDTLKFVTEQ AK GA (SEQ. ID NO: 30)
YRALVDTEFKVKQEAGAK (SEQ. ID NO: 31)
RALVDTEFKVKQEAGAK (SEQ. ID NO: 32)
YRAL V DTLKFV TQ AE GAK (SEQ. ID NO: 33)

II. peptides Targeted to Infections and Atherosclerotic Plaque

VGVAPGVGVAPGVGVAPG (SEQ. ID NO: 34)
VPGVGVPGVGVPGVGVPGVG (SEQ. ID NO: 35)
formyl Nleu.LF.Nle.YK (SEQ. ID NO: 36)
formyl MIFL (SEQ. ID NO: 37)
formyl MLFK (SEQ. ID NO: 38)
formyl MLFI (SEQ. ID NO: 39)
formyl MFIL (SEQ. ID NO: 40)
formyl MFLI (SEQ. ID NO: 41)
formyl MLIF (SEQ. ID NO: 42)
formyl MILF (SEQ. ID NO: 43)
TKPR (SEQ. ID NO: 44)
VGVAPG (SEQ. ID NO: 45)
formyl MLF
YIGSR (SEQ. ID NO: 46)
$CH_3CO$. YIGSRC (SEQ. ID NO: 47)

III. Thrombus

NDGDFEEIPEEYLQ (SEQ. ID NO: 48)
NDGDFEEIPEEY ($SO_3Na$) LQ (SEQ. ID NO: 49)
GPRG (SEQ. ID NO: 50)

IV. Platelets

D-Phe.PRPGGGGNGDFEEIPEEYL (SEQ. ID NO: 51)
RRRRRRRRGDV (SEQ. ID NO: 52)
PLYKKIIKKLLES (SEQ. ID NO: 53)
RGD
RGDS (SEQ. ID NO: 54)

V. Alzheimers Disease (Amyloid Plaque)

EKPLQNFTLSFR (SEQ. ID NO: 55)

It should be further understood that the polypeptides described above may be obtained in a number of ways, including isolation from natural sources, synthetically, semisynthetically, or by DNA recombinant methods.

5.3. Metallic Complexes of the Polypeptide Constructs

The constructs of the present invention are best utilized as their metallic complexes for either diagnostic or therapeutic applications. Thus, a complex of the formula (II) is contemplated:

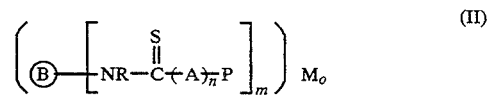

(II)

in which,

"B" is a saturated or unsaturated aliphatic or aromatic hydrocarbon backbone comprising 1-20 carbon atoms and, optionally, one or more heteroatoms selected from the group consisting of nitrogen, oxygen, phosphorus and sulfur;

"P" is a polypeptide comprising 2-100 amino acids, the polypeptide capable of targeting particular cells, tissues or organs of the body;

"A" may be the group —NR'—NR"— or the group —NR'—NR"—L— in which L may be an aliphatic or aromatic linker group comprising 1-12 carbon atoms and, optionally, one or more heteroatoms selected from the group consisting of nitrogen, oxygen, phosphorus and sulfur;

R, R', and R" may be the same or different and may be hydrogen or an aliphatic group comprising 1-6 carbon atoms and, optionally, one or more heteroatoms selected from the group consisting of nitrogen, oxygen, phosphorus and sulfur;

m is an integer $\geq 2$, provided that the groups R, R', R'', L and "P" of a given chain may be the same or different from the groups R, R', R'', L and "P" of another chain;

n is an integer $\geq 0$, $\leq 2$;

o is an integer $\geq 1$, $\leq m$;

"M" is a metallic moiety;

or a pharmaceutically acceptable salt thereof.

As will be apparent to those of ordinary skill in the art, many types of metals, in different oxidation states (e.g., 1+, 2+, 3+, etc.) or chemical states (oxo, dioxo, trioxo, hydroxy, sulfide, nitride, etc.), may be complexed by a variety of coordinating or chelating agents. However, certain metals coordinate more strongly with sulfur containing substituents, and these metals are preferred. Preferably the metal is a radiometal, i.e., a radioactive isotope of a coordinate metal. Such metals are useful as imaging agents in diagnosis, and as therapeutic agents for targeted radiotherapy. In other cases, the metal is simply one that is toxic to the target cell.

Most advantageously, a metallic moiety comprises a cationic metal selected from the group consisting of transition metal elements, lanthanide metal elements, and actinide metal elements. As mentioned above, preferred metals are those that are radioisotopes but, also, paramagnets. Representative metals, both diagnostic and therapeutic, of potential use in the complexes and methods of the present invention include, but are not limited to, those presented in Table II, below:

TABLE II

| Representative Metals For Use In Complexes | |
|---|---|
| | Half life |
| Diagnostic Radionuclide | |
| Ruthenium-97 | 2.9 d |
| Technetium-99m | 6.0 h |
| Mercury-197 | 2.7 d |
| Gallium-67 | 77.9 h |
| Gallium-68 | 1.1 h |
| Osmium-191 | 15 d |
| Indium-111 | 2.6 d |
| Indium-113m | 1.7 h |
| Lead-203 | 52 h |
| Therapeutic Radionuclide | |
| Palladium-105 | 17.0 d |
| Silver-111 | 7.3 d |
| Antimony-119 | 1.6 d |
| Gold-198 | 2.7 d |
| Gold-199 | 3.1 d |
| Copper-67 | 2.6 d |
| Rhenium-186 | 88.9 h |
| Rhenium-188 | 16.7 h |
| Bismuth-212 | 1.0 h |

In addition, the following metals any also be useful in the present invention: paramagnets ($Gd^{3+}$, $Fe^{3+}$, $Mn^{2+}$, $Cr^{2+}$), fluorescent metals ($Eu^{3+}$), position-emitting metals ($^{68}Ga$, $^{62}Cu$, $^{52}Fe$, $^{62}Zn$), diagnostic gamma-emitters ($^{169}Yb$), therapeutic beta-emitters ($^{90}y$, $^{169}Er$, $^{121}Sn$, $^{127}Te$, $^{143}Pr$, $^{165}Dy$, $^{32}P$, $^{142}Pr$), therapeutic alpha-emitters ($^{211}At$), and even non-radioactive heavy metal toxins (Zn, Pt).

The metal complexes of the targeted polypeptide constructs of the present invention can be prepared by bonding the metal ion directly to the construct. Conventional methods of attaching metal ions to chelating agents may be utilized to accomplish binding. Generally, reduced pertechnetate (technetium thought to be in the form of Tc(III), Tc(IV) or Tc(V), or any combination thereof), reduced perrhenate (rhenium thought to be in the form of Re(III), Re(IV), or Re(V), or any combination thereof), copper (generally Cu(II), Cu(I), mercury (Hg(I) or Hg(II), or both) or lead (Pb(II) or Pb(IV), usually) are preferred metal ions for chelation with the targeted peptide systems of the invention. Examples of radiometals for chelation are technetium-99m (Tc-99m), copper-67 (Cu-67), rhenium-186 (Re-186), and-188 (Re-188), silver 111 (Ag-111), mercury 197 (Hg-197), lead 212 (Pb-212) and bismuth 212 (Bi-212). Bi-212 is the decay product of Pb-212. With a half-life of about 10.6 hours, Pb-212 rapidly decays to Bi-212, which in turn rapidly decays (half-life of about 1 hour) with emission of an alpha particle. Other metal ions, such as indium (particularly In-III) and the lanthinide ions (generally Ln(III), and in particularly gadolinium Gd(III)) are also useful. Hence, the metal, if desired, may be a positron gamma, alpha or beta particle emitter.

An advantage of the instant constructs is their stability. Hence, a targeted polypeptide construct can be prepared and stored prior to complexation, including chelation, with a metal ion. The ability to store the targeted polypeptide constructs makes large scale production and distribution possible, and allows for lot-to-lot uniformity analysis and quality control.

Technetium labeling of the chelator is effected by conventional procedures. In a preferred embodiment, reduced Tc-99m is added to the conjugate as Tc-99m-GLUCOSCAN® (DuPont, North Billerica, Mass.), using established methods (e.g., Dswanjee, Seminar in Nuclear Medicine (1990) 20:5–27).

In another embodiment, pertechnetate can be obtained from commercial sources, usually as $NH_4TcO_4$ or $NaTcO_4$ in ionic aqueous solution. Other forms of pertechnetate can be used, with appropriate modification of the complexation procedure. Reduction of the pertechnetate can be accomplished with a variety of reducing agents, for example, stannous ion, dithionite, borohydride, ferrous ion, and the like, in aqueous, non-aqueous or aqueous-organic liquid mixtures, buffered at about pH 4 to about pH 7. The reducing agent, preferably stannous ion, should be added in excess to ensure complete reduction of the pertechnetate. Preferably, the reduction is effected under an inert gas atmosphere, e.g., nitrogen or argon, at about room temperature. The reduced pertechnetate is then allowed to react with the targeted polypeptide construct. Unbound technetium can be removed, if necessary, from the targeted polypeptide construct by simple techniques, e.g., gel filtration chromatography, reverse phase chromatography, or ion exchange chromatography, depending on the molecular weight, hydrophobic, and ionic characteristics of the compounds or complexes.

Rhenium labeling can be effected in substantially the same way as technetium labeling. With rhenium, however, special care must be taken to exclude oxygen from the system.

Copper labeling can be effected by use of a copper ion salt, usually Cu(II) ions with counterions such as chloride, citrate, tartate, acetate and the like. Similarly, mercuric or lead salts can be "complexed" in a manner analogous to copper. Presently, $^{67}CuCl_2$, $^{197}HgCl_2$, and $^{197}Hg(NO_3)_2$ are available on contract order from radioisotope suppliers. For example, Oak Ridge National Laboratories is one source of these compounds. Bismuth-212 is usually obtained from decay of lead-212.

Thus, a lead-212 complex is allowed to decay to form the bismuth-212 complex.

5.4. Compounds Useful as Intermediates

The present invention also makes use of certain compounds which can be prepared and isolated separate from the compounds of the formula (I). These compounds include the compounds of the formula (III):

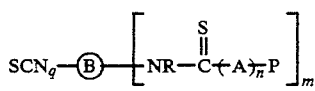

(III)

in which,

"B" is a saturated or unsaturated aliphatic or aromatic hydrocarbon backbone comprising 1–20 carbon atoms and, optionally, one or more heteroatoms selected from the group consisting of nitrogen, oxygen, phosphorus and sulfur;

"P" is a polypeptide comprising 2–100 amino acids, the polypeptide capable of targeting particular cells, tissues or organs of the body;

"A" may be the group —NR'—NR"— or the group —NR'—NR'—L— in which L may be an aliphatic or aromatic linker group comprising 1–12 carbon atoms and, optionally, one or more heteroatoms selected from the group consisting of nitrogen, oxygen, phosphorus and sulfur;

R, R', and R" may be the same or different and may be hydrogen or an aliphatic group comprising 1–6 carbon atoms and, optionally, one or more heteroatoms selected from the group consisting of nitrogen, oxygen, phosphorus and sulfur;

m is an integer $\geq 1$, provided that the groups R, R', R", L and "P" of a given chain may be the same or different from the groups R, R', R", L and "P" of another chain;

n is an integer $\geq 0$, $\leq 2$;

q is an integer $\geq 1$;

or a pharmaceutically acceptable salt thereof.

These intermediates are useful in the preparation of the compounds of formula (I), especially those in which different, polypeptide chains are desired. Such "hetero" polyvalent constructs could be designed, for example, to target two separate receptors that are expressed by a great majority of a given class of cells. In other words, receptor-A may only be expressed by 80 percent of certain tumor cells, while receptor-B may likewise be expressed by 60 percent of the same tumor cells. However, the two populations may be only partially overlapping such that the combined proportion of tumor cells that express either receptor-A or receptor-B may be 95 percent of the entire tumor cell population. Thus, a higher percentage of tumors can be successfully targeted by incorporating separate polypeptides that target receptors A and B, respectively, in a single construct.

5.5. Some Uses of Metallated Targeted Polypeptide Constructs

The metal complexes of the constructs of the present invention are useful in a variety of therapeutic and diagnostic applications.

In one embodiment, the targeting peptide is a CDR of a monoclonal antibody specific for a tumor antigen for use in imaging tumors. In specific embodiments, the CDR is derived from an antibody that is reactive with a tumor cell, preferably a human tumor cell. For example, the antibody can be a monoclonal antibody reactive with human mammary tumor cells (Colcher et al., Proc. Natl. Acad. Sci. U.S.A,. (1981) 78:3199–3203), e.g. monoclonal antibody B72.3. In another embodiment, the antibody can be a monoclonal antibody specific for a marker for prostatic cancer (U.S. Pat. No. 5,162,504; Horoszewicz et al., Cancer Res. (1987) 7: 927–936), i.e., monoclonal antibody 7E11. In yet a further embodiment, the antibody can be a monoclonal antibody specific for a colorectal cancer antigen (Granowska et al., Int. J. Colorect. Dis. (1989) 4:97–108), e.g., monoclonal antibody C46. The foregoing are provided as specific examples of antibodies having CDRs for use as targeting peptides, and the invention is not limited to those examples. Other antibodies are known in the art and their peptide CDRs can be used as targeting peptide of the present invention.

In another embodiment, the targeting polypeptide is a peptide useful for imaging thrombotic clots. Hence, the peptide of the amino acid sequence SYRGDVRGDF-NH$_2$ (SEQ. ID NO: 17) (i.e., the carboxy terminus, F, is amidated) is particularly useful in this application. Other polypeptides useful in the present invention have been described previously, supra.

In in vivo diagnostic applications, specific tissues or even specific cellular disorders may be imaged by administration of a sufficient amount of a metallated targeted polypeptide construct of the instant invention.

A wide variety of metal ions suitable for in vivo tissue imaging have been tested and utilized clinically. For imaging with radioisotopes, the following characteristics are generally desirable: (a) low radiation dose to the patient; (b) high photon yield which permits a nuclear medicine procedure to be performed in a short time period; (c) ability to be produced in sufficient quantities; (d) acceptable cost; (e) simple preparation for administration; and (f) no requirement that the patient be sequestered subsequently. These characteristics generally translate into the following: (a) the radiation exposure to the most critical organ is less than 5 rad; (b) a single image can be obtained within several hours after infusion; (c) the radioisotope does not decay by emission of a particle; (d) the isotope can be readily detected; and (e) the half-life is less than four days (Lamb and Kramer, "Commercial Production of Radioisotopes for Nuclear Medicine" In Radiotracers For Medical Applications, Vol. 1, Rayudu (Ed.), CRC Press, Inc., Boca Raton, pp. 17–62). Preferably, the metal is technetium-99m.

By way of illustration, the targets that one may image include any solid neoplasm, certain organs such as lymph nodes, parathyroids, spleen and kidney, sites of inflammation or infection (e.g., macrophages at such sites), myocardial infarction or thromboses (neoantigenic determinants on fibrin or platelets), and the like evident to one of ordinary skill in the art. Furthermore, the neoplastic tissue may be present in bone, internal organs, connective tissue, or skin.

As is also apparent to one of ordinary skill in the art, one may use the present invention in in vivo therapeutics (e.g., using radiotherapeutic metal complexes), especially after having diagnosed a diseased condition via the in vivo diagnostic method described above, or in in vitro diagnostic application (e.g., using a radiometal or a fluorescent metal complex).

Pharmaceutical compositions comprising the compounds or complexes of the present invention can be prepared using appropriate pharmaceutically acceptable carriers, excipients, diluents and adjuvants. As used herein, the term "pharmaceutically acceptable" means approved by a regulatory agency of the Federal or a state government or listed in the U.S. Pharmacopeia or other generally recognized pharmacopeia for use in animals, and more particularly in humans. Such pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutically acceptable excipients include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like.

These compositions can take the form of solutions, suspensions, tablets, pills, capsules, powders, sustained-release formulations and the like. Suitable pharmaceutically acceptable carriers are described in "Remington's Pharmaceutical Sciences" by E. W. Martin.

Such compositions will contain an effective therapeutic or diagnostic amount of the active compound or complex together with a suitable amount of carrier so as to provide the form for proper administration to the patient. While intravenous injection is a very effective form of parenteral administration, other modes can be employed, including but not limited to intramuscular, intraventricular, intra-arteriole, intraperitoneal, and subcutaneous injection, along with oral and nasal administration. In another embodiment, the invention can be administered topically or locally by infusion or direct application.

The therapeutic agents and diagnostic agents of the instant invention may be used in methods for the treatment and/or diagnosis of diseases in animals, and more preferably, mammals, including humans, domesticated animals or livestock.

Accordingly, a method of obtaining an image of an internal region of a subject is contemplated in the instant invention which comprises administering to a subject an effective amount of the construct of interest in which the metal is radioactive, and recording the scintigraphic image obtained from the decay of the radioactive metal. Likewise, a method is contemplated of enhancing an MR image of an internal region of a subject which comprises administering to a subject an effective amount of the complex of a construct of interest in which the metal is paramagnetic, and recording the MR image of an internal region of the subject.

Other methods include a method of enhancing a sonographic image of an internal region of a subject comprising administering to a subject an effective amount of the construct of interest, and recording the sonographic image of an internal region of the subject. In this latter application, the metal is preferably any non-toxic heavy metal ion. A method of enhancing an X-ray image of an internal region of a subject is also provided which comprises administering to a subject an effective amount of the complex of a construct of interest, and recording the X-ray image of an internal region of the subject. A radioactive, non-toxic heavy metal ion is preferred.

A pharmaceutical kit can be prepared comprising a predetermined amount of the compound of formula (I) and, optionally, a pharmaceutically acceptable carrier, stabilizer, or preservative. A preferred kit would further comprise a predetermined amount of a reducing agent and a stabilizer that includes a transchelator. A transchelator as used herein denotes a chelating agent that is "weaker" than the constructs of the present invention. Thus, the transchelator stabilizes the reduced species of pertechnetate while allowing the construct to form a stable complex with the reduced metal. Suitable transchelators may be alkylenepolyaminocarboxylic acid compounds, such ethylenediaminetetraacetic acid (EDTA), hydroxyethylenediaminetriacetic acid (HEDTA), sodium glucoheptonate, sodium tartrate, sodium gluconate, sodium saccharate or sodium 1,1,3,3-propylenetetraphosphonate. Depending on the nature of the metal eventually chosen, the kit can be used to prepare a radiodiagnostic agent or a radiotherapeutic agent.

As a further illustration of the present invention, the following description of specific examples is provided. However, the following description should not be construed as limiting the invention in any way.

6. EXAMPLES

6.1 Preparation Of Diisothiocyanatobenzoic Acid, 2

A 500 mL one-neck round bottom flask was charged with 15.2 g (0.10 mol) of 3,5-diaminobenzoic (Aldrich), 175 mL of chloroform and 175 mL of water. Then, 17.0 mL (0.23 mol) of thiophosgene (Aldrich)was added to the resultant slurry at room temperature over a period of 15 min. The two phase, orange-red reaction mixture was allowed to stir for an additional 6 h at ambient temperature and then the aqueous layer was separated from the organic layer. The aqueous layer was extracted with two 100 mL portions of chloroform and then the organic layers were combined and washed with three 400 mL portions of water. The chloroform solution was dried over anhydrous magnesium sulfate, filtered, and the solvents were evaporated from the filtrate under vacuum to give 20.7 g (77 mmol, 88% yield) of 3,5-diisothiocyanatobenzoic acid, 2; mp 125°–127° C.; $^1$H NMR (CDCl$_3$, TMS): δ 7.81 (s, 2H), 7.27 (s, 1H).

6.2. Benzoic acid bis-thiourea derived from Neuromedin-C (SEQ. ID NO: 56), 3, and isothiocyanatobenzoic acid mono-thiourea derived from Neuromedin-C (SEQ. ID NO: 56), 4

A 20 mL conical reaction vial equipped with a magnetic stir vane was charged with 2 mL of N,N-dimethyformamide (DMF), 42 mg (37.5 μmol) of Neuromedin C (NMc, H-Gly-Asn-His-Trp-Ala-Val-Gly-His-Leu-Met-NH$_2$, (SEQ. ID NO: 56) 1), 3.5 mg (16.8 μmol) of 3,5-diisothiocyanatobenzoic acid, 2, 10 mL of water, and 10 μL of N,N-diisopropylethylamine (DIEA). The vial was sealed and the light orange reaction mixture was allowed to stir at room temperature (RT) for 20 h. The reaction solvents were then removed by rotary evaporation and 10 mL of 30% acetonitrile in water was added to the distillation residue to give a slightly cloudy solution. The two major products, 3 (17.0 mg, 6.8 μmol, 41% yield) and 4 (10.8 mg, 8.0 μmol, 47% yield) were then isolated by several 2 mL injections of this solution onto a semi-preparative (2.5 cm diameter×30 cm length) Waters Novapak C-18

HPLC column followed by gradient elution with water/acetonitrile. Mass spectral analysis of samples of 3 and 4 gave molecular ions of 2476.5 and 1356.5, respectively. Calculated molecular weights are 2476.89 and 1356.58, respectively.

6.3. Radiolabeling Of Compound, 3 (SEQ. ID NO: 56)

Compound 3 incorporates 73% of Tc-99m (50 μCi/μg), as detected by instant thin layer chromatography (ITLC). For labeling this peptide construct, Glucoscan-Tc-99m (50 μCi/μg) was mixed with 40 μg/mL of peptide in NaAc buffer at pH 5.0, 37° C. for 1 hour. Two microliters of the incubated material were spotted onto a silica gel impregnated ITLC glass fiber sheet (Gelman). The ITLC sheet is then placed into a 10 mL glass vial containing 1.5 mL of 0.9% saline solution. The chromatography was allowed to proceed for 1.5 min and the ITLC strip was then removed and allowed to dry. The strip was cut in half, and both the top and bottom portions were counted in a LKB gamma radiation counter. The percent of gamma radiation remaining on the bottom of the ITLC strip was designated as the "percent incorporation."

6.4. Preparation of Benzoic acid bis-thiosemicarbazide derived from N-acetyl-Neuromedin C-hydrazide, (SEQ. ID NO: 56), 6

A 200 mL conical reaction vial equipped with a magnetic stir vane was charged with 10 mL of DMF, 100 mg (85 μmol) of N-acetyl-Neuromedin C-hydrazide (SEQ. ID NO: 56) 200 ul of DIEA and 10 mg (40 μmol) of 3,5-diisothiocyanatobenzoic acid, 2. The flask was sealed and the reaction mixture is allowed to stir for 16 h at RT. The solvents were then removed by rotary evaporation and 33 mL of 10% acetonitrile in water was added to the colorless distillation residue to give a cloudy solution. The product 6 (55 mg, 21 μmol, 53% yield) was obtained by several 2 mL injections of this solution onto a semi-preparative (2.5 cm dia.×30 cm length) Waters Novapak C-18 HPLC column followed by gradient elution with water/acetonitrile. Mass spectral analysis of a sample of 6 gave a molecular ion of 2590.6. The calculated molecular weight is 2591.01.

Two radiolabeled preparations of 6 are obtained according to the method described above; one was labeled with 61.7% Tc-99m and the other labeled with 98.5%

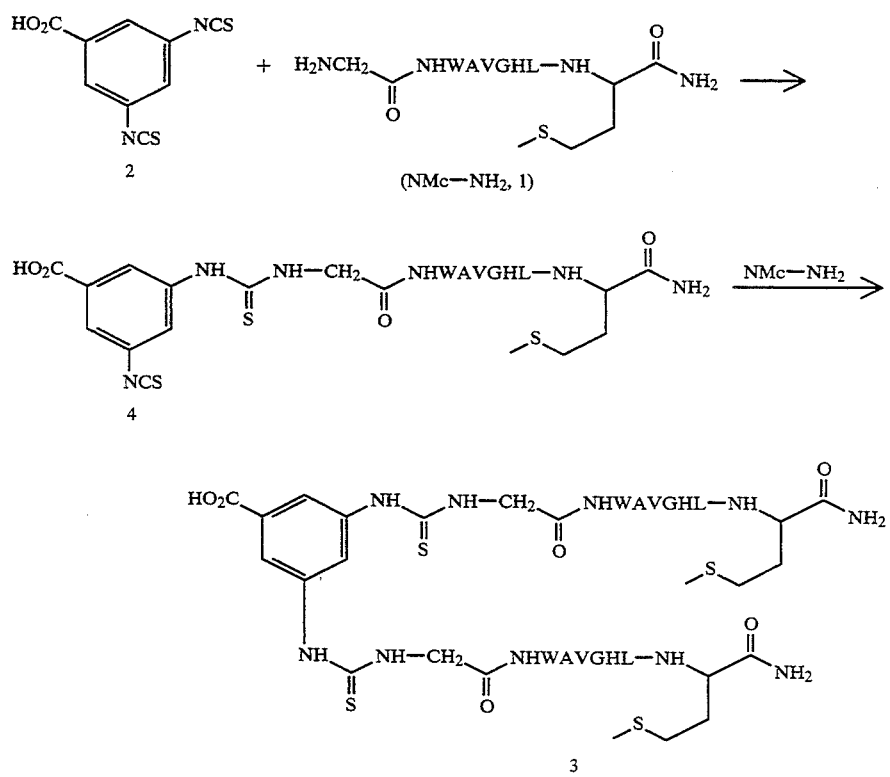

NHWAVGHL=Amino Acid Abbreviations

Tc-99m (50 μCi/μg), as detected by ITLC.

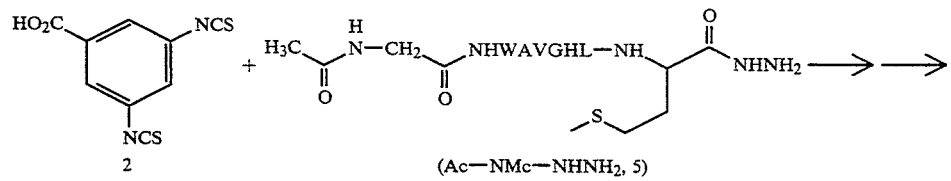

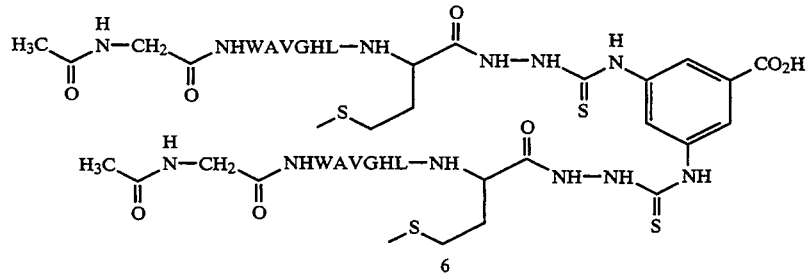

NHWAVGHL = Amino Acid Abbreviations

6.5. Preparation of Lysine-(epsilon-Neuromedin C-thiourea)-alpha-Neuromedin C-thiohydantoin, 9

6.5.1. Preparation of 1-Carboxy-1,5-diisothiocyanatopentane, 8

A solution of NaHCO$_3$ (21.62 G, 94.36 mmol) in water was added to a suspension of lysine methyl ester dihydrochloride, 7, (10.0 G, 257 mmol) in dry THF (250 mL) and the resulting biphasic mixture was cooled to 0° C. Thiophosgene (7.2 mL, 94.36 mmol) was introduced dropwise and the mixture was stirred at 0° C. for 2 h. EtOAc (50 mL) was added and the aqueous phase is removed. The organic layer is washed twice with 1N aqueous HCl, once the water, and once with saturated NaCl, and dried over MgSO$_4$. Concentration gives 10,19 g (97%) of a light yellow oil. $^1$H NMR (CDCl$_3$) δ 4.32 (t, 1HJ=6.5Hz), 3.83 (s,3H), 3.58 (t, 2H,J)=6.5 Hz), 1.97 (m, 2H), 1.75 (m, 2H), 1.60 (m, 2H).

6.5.2. Preparation of Lysine-(epsilon-Neuromedin C-thiourea)-alpha-Neuromedin C-thiohydantoin, 9

Neuromedin C (16 mg, 13 μmol) is dissolved in dry DMF (120 μL) and e (3.2 mg, 13 μmol) was added, followed by N,N-diisopropylethylamine (2.3 μL, 13 μmol), and the mixture was incubated at room temperature. After three hours N,N-diisopropylethylamine (5 μL) was added. The adduct containing two molecules of neuromedin C was isolated by preparative reversed-phase HPLC after twenty hours reaction time. A linear gradient of 5% to 90% CH$_3$CN in water containing 0.1% CF$_3$COOH over 80 minutes was utilized. Fractions containing the product were concentrated in vacuo and the residue was lyophilized to provide the peptide adduct. Analytical HPLC on a C18 HPLC column using the same gradient demonstrated a purity of 79%. FAB$^+$ MS m/a 2453 (M+H)$^+$.

Compound 9 was labeled subsequently with 74% Tc-99m (50 μCi/μg), as detected by ITLC.

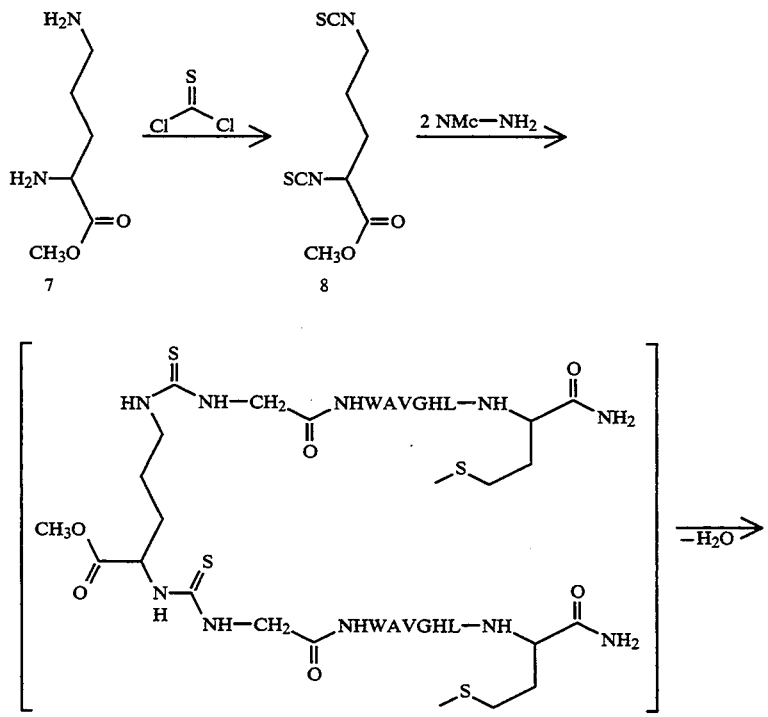

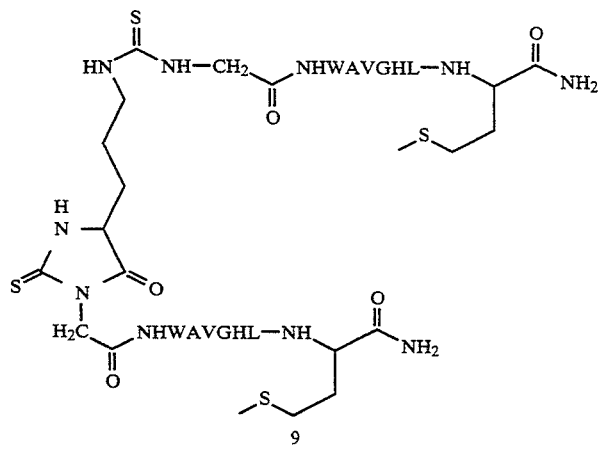

NHWAVGHL = Amino Acid Abbreviations

6.6. Preparation of Benzoic acid mono-thiourea monothiosemicarbazide derived from Neuromedin C-hydrazide, (SEQ. ID NO: 56) 12

6.6.1. Preparation of Adduct, 11 (SEQ. ID NO: 56)

A 20 mL reaction vial equipped with a micro stir bar is charged with 10 umoL of Fmoc-NMc-NHNH2(SEQ. ID NO: 56), 10, 5 mL of N,N-dimethylformamide, 100 umoL of N,N-diisopropylethyl amine, and then 10 umoL of 3,5-diisothiocyanatobenzoic acid, 2. The reaction mixture is stirred at 22°–24° C. for 3h and the solvents are then distilled away on a rotary evaporator. The resultant residue is dissolved in 10% acetonitrile in water and the desired adduct, 11, is isolated from this solution by C-18 semi-preparative scale HPLC using a mixture of acetonitrile in water (0.1% TFA) as eluent. The solvents are evaporated from the collected chromatography fractions under reduced pressure to leave purified adduct, 11, as white residue.

6.6.2. Intramolecular Cyclization of Adduct, 11

A 20 mL reaction vial equipped with a micro stir bar is charged with 10 umol of adduct 11, 5mL of N,N-dimethylformamide, and 100 umoL of piperidine, D. The reaction mixture is then allowed to stir at 22°–24° C. for a further 24 h. The solvents are then removed by rotary evaporation to leave a distillation residue which is dissolved in 10% acetonitrile in water. The desired construct 12 is isolated from this solution by semi-preparative C-18 HPLC using a mixture of acetonitrile in water (0.1% TFA) as eluent. The solvents are evaporated away from the chromatography fractions to leave purified construct 12 as a waxy solid.

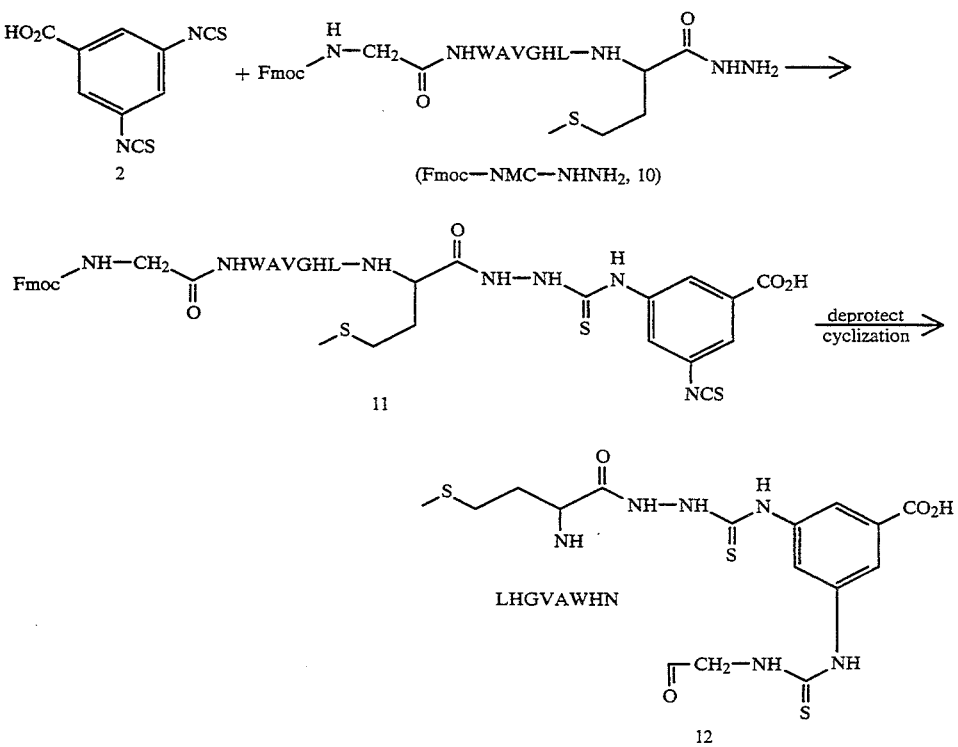

NHWAVGHL = Amino Acid Abbreviations

6.7. In Vitro Receptor Binding Assay Experiments

6.7.1. Materials and Methods

Murine NIH-3T3 fibroblast cells (ATCC No. CCL92) were released from flasks with EDTA harvest buffer, consisting of 0.6 mm EDTA, 25 mm PBS (8 g NaCl, 0.2 g KCl, 1.44 g $Na_2PO_4$, 0.2 g $KH_2PO_4$ per liter), pH 7.4, 37° C., by incubation for 15 min.

The cells were washed twice with Assay Buffer (50 mM Tris-HCl, 100 mM NaCl, 0.1% BSA, 0.1 mg/mL bacitracin, 0.05 mg/mL aprotinin, 1 mM PMSF), pH 7.4, 4° C. and resuspended at a density of $3 \times 10^6$ cells/mL.

A 0.5 mL Eppendorf tube was prepared for each assay point by incubating the tube overnight with a blocking solution of 1% BSA, 50 mM Tris. HCl, 100 mM NaCl, pH 7.4. The blocking solution was removed.

Each tube was charged with $4 \times 10^4$ cells. Aliquots of compound 3, compound 6 and Neuromedin C (Bachem, Bubendorf, Switzerland) at 1, 10 and 100 nM were mixed with assay buffer, cells, and $^{125}$I-GRP (Amersham) to make 150 μL aliquots containing 0.45pm $^{125}$I-GRP. Three control tubes with no cells or competitor were prepared for measurement of total counts added.

The samples were incubated for 30 min at RT. The contents of each tube were transferred into the wells of a 96-well filter bottom plate (Millipore Multiscreen, Arlington Heights,. Mass.) and filtered under moderate vacuum (water aspirator). Each filter was washed three times by filling each well with ice cold PBS, Ph 7.4, 0.1% BSA. The plate was allowed to dry. Dried filters were placed into gamma-counter tubes ($12 \times 75$ mm glass). The radioactivity on each filter and in the control tubes was counted using a LKB gamma counter. The bound/total added for each assay tube was calculated.

6.7.2. Results

Inhibition of binding of labeled GRP to the NIH-3T3 cells is reported in Table III. The binding assay yielded an $IC_{50}$ of compound 3 of 10.6 nM, and an $IC_{50}$ of compound 6 of 43.3 nM. Thus, the competing ligands (compounds 3 and 6) to $^{125}$I-GRP bound within an order of magnitude of the control ligand Neuromedin C.

TABLE III

Inhibition of Binding of I-125-GRP to NIH-3T3 Cells

| I-125-GRP | INHIBITOR | AVG CPM BOUND | % BOUND | % INHIBITION |
|---|---|---|---|---|
| 0.45 pM | None | 3,905 | 5.9 | 0 |
| 0.45 pM | 1 nm NMc* | 1,420 | 2.2 | 63 |
| 0.45 pM | 10 nm NMc | 1,126 | 1.7 | 71 |
| 0.45 pM | 100 nm NMc | 940 | 1.4 | 76 |
| 0.45 pM | 1 nm Compound 3 | 2,601 | 3.9 | 34 |
| 0.45 pM | 10 nm Compound 3 | 1,415 | 2.1 | 64 |
| 0.45 pM | 100 nm Compound 3 | 1,056 | 1.6 | 73 |
| 0.45 pM | 1 nm Compound 6 | 2,993 | 4.4 | 26 |
| 0.45 pM | 10 nm Compound 6 | 2,163 | 3.3 | 44 |
| 0.45 pM | 100 nm Compound 6 | 1,264 | 1.9 | 68 |

*Neuromedin C

6.8. In Vivo Studies

6.8.1. Animal Models and General Methods

Biodistribution and imaging studies were conducted using female Nu/Nu HT-29 xenograft tumor-bearing mice, a model for colon carcinoma. Compounds 3 and 6 were examined in the experiments. Two μg of the test compounds were labeled with 100 μCi of Tc-99m and each was injected into 10 Nu/Nu mice bearing HT-29 tumors on the flank. The organs of interest were removed from half the mice at 3 hr, and the organs of the remaining mice were removed at 22 h. Each set of organs were counted for gamma radiation.

6.8.2. Preparation of Radiolabeled Constructs

Twenty μg of each construct was dissolved in 20 mM sodium acetate, pH 4.5, at a minimum concentration of 30 μg/mL. The pH was checked and adjusted as necessary. A 50 mCi vial of $^{99m}TcO_4Na$ (Syncor) was added to a vial of Glucoscan® (Dupont) in a leaded glass shield using a shielded tuberculin syringe. 100 μL of the resulting solution was dose calibrated, and the volume required for 20 doses of 100 μCi was calculated (ca. 40–45 μL). This amount was divided into two equal parts and added to the two solutions of construct in microfuge tubes and incubated for 1 h at 37° C. Percent chelation was checked by chromatography on ITLC developed with 0.9% saline, and analyzed by autoradiography counter. The two solutions were diluted to 2.2 mL each with 0.9% saline. The diluted solutions were then divided into numbered tuberculin syringes (200 μL each). The air was then removed. Four 10 μL aliquots of each dosage were saved in 12 x 75 mm tubes for counting with the animal parts.

6.8.3. Pharmacokinetics

The Tc-99m labeled Compound 3 and Tc-99m labeled Compound 6 were injected intravenously (about 2.0 μg/mouse or about 200 μC:/mouse) on day 0 into 2 groups each of 5 Nu/Nu mice (each weighted about 25–30 mg) bearing measurable subcutaneous tumors. At 3 and 23 hours post injection, one group of mice injected with labeled 3 and one group of mice injected with labeled 6 are dissected for biodistribution determinations. Immediately prior to dissection, tumor-bearing mice were imaged using a Starcam II gamma camera (General Electric, Milwaukee, Wis.). Based on the gamma camera image and biodistribution studies, the labeled Neuromedin C peptide constructs were able to bind specifically to the target tumor.

Dissected tissues were weighed, and their content of Tc-99m was determined by gamma counting. The data are presented below as the ratio of the cpm/g in each organ compared to the cpm/g in blood (organ:blood ratio) and the percentage of the injected dose (ID)/g in each organ.

6.8.4. Results

The biodistribution and imaging efficacy of Tc-99m labeled 3 and Tc-99m labeled 6 in nude mice bearing HT-29 colon carcinoma xenografts was assessed at 3 and 22 hours after i.v. injection, The average dose injected contained ~200 μCi on 2 μg of Compound 3 or Compound 6. Compound 3 is a bis-neuromedin C construct derivatized at the N-terminus, while the Compound 6 is a bis-neuromedin C construct derivatized at the C-terminus.

Figure 2:
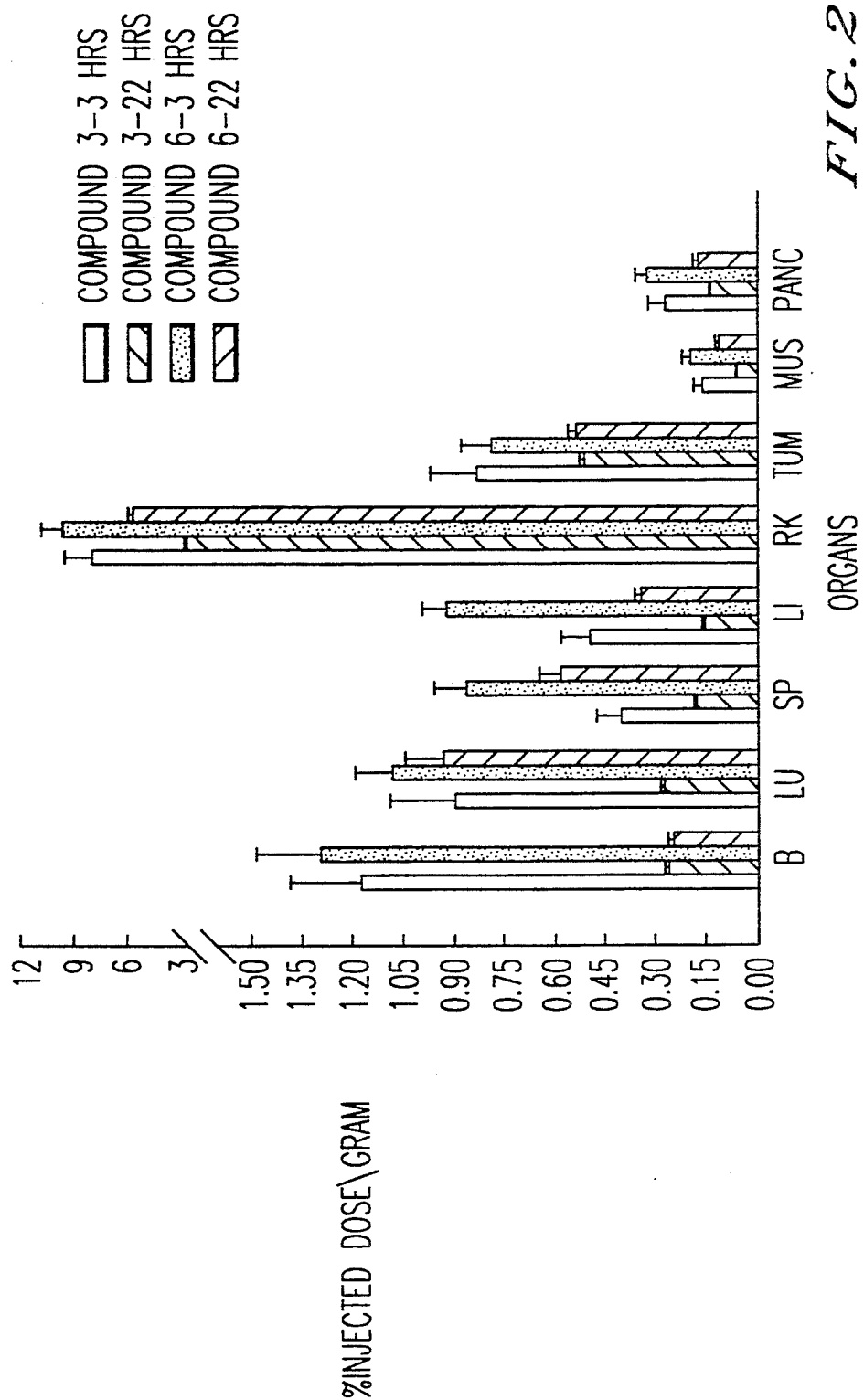
FIG. 2 presents the results of the biodistribution study of FIG. 1, reported as the percentage of the total amount of radioactivity of the injected dose found per gram of each organ (%ID/g). The organs are abbreviated as in FIG. 1, and the bars have the same meaning. Compound 3 at 22 hrs had a tumor localization percentage of 0.51%ID/g, which is higher than any other organ except the kidneys and means that good scintigraphic contrast between tumor and other tissues will generally be obtained. Because the compound is cleared by the kidneys, a high %ID/g value in that organ is always observed. It is also important to note that a greater drop in % ID/g from 3 hrs to 22 hrs is observed in all the normal organs relative to the tumor. This observation indicates a greater rate of clearance of compound or complex, which is non-specifically bound to normal organs, compared with the rate of clearance from tumor.

Localization of labeled 3 to HT-29 tumors was evident at 22 hours after injection. The tumor:blood ratio was 2.0:1 (Table IV, FIG. 1) and the average accumulations in HT-29 tumors was 0.51% ID/g (Table V, FIG. 2). Similarly, localization of labeled 6 to tumors was evident at 22 hours after injection when the average accumulation in tumors was 0.38% ID/g (Table V, FIG. 2) and the corresponding tumor:blood ratio was 2.3:1 (Table IV, FIG. 1).

TABLE IV

| | Biodistribution of $^{99m}$Tc-Labeled Constructs Organ to Blood Ratio | | | | | | | |
|---|---|---|---|---|---|---|---|---|
| | 3 | | | | 6 | | | |
| Organ | 3 HR. AVG | s.e.m. | 22 HR. AVG | s.e.m. | 3 HR. AVG | s.e.m. | 22 HR. AVG | s.e.m. |
| Blood | 1.00 | 0.00 | 1.00 | 0.00 | 1.00 | 0.00 | 1.00 | 0.00 |
| Lung | 0.76 | 0.06 | 1.07 | 0.03 | 0.87 | 0.06 | 3.80 | 0.19 |
| Spleen | 0.34 | 0.01 | 0.69 | 0.04 | 0.72 | 0.09 | 2.40 | 0.11 |
| Liver | 0.42 | 0.01 | 0.61 | 0.0.4 | 0.76 | 0.07 | 1.45 | 0.16 |
| Kidney-R | 6.86 | 0.15 | 9.84 | 0.32 | 8.51 | 0.92 | 24.22 | 1.68 |
| Kidney-L | 7.01 | 0.03 | 9.73 | 0.45 | 9.24 | 0.74 | 25.44 | 2.08 |
| Tumor | 0.71 | 0.01 | 2.00 | 0.16 | 0.62 | 0.04 | 2.25 | 0.12 |
| Muscle | 0.14 | 0.01 | 0.22 | 0.01 | 0.15 | 0.01 | 0.45 | 0.01 |
| Pancreas | 0.23 | 0.01 | 0.50 | 0.03 | 0.25 | 0.02 | 0.70 | 0.02 |

TABLE VI

| | Percent Of Injected Dose | | | | | | | |
|---|---|---|---|---|---|---|---|---|
| | 3 | | | | 6 | | | |
| Organ | 3 HR. AVG | s.e.m. | 22 HR. AVG | s.e.m. | 3 HR. AVG | s.e.m. | 22 HR. AVG | s.e.m. |
| Blood | 1.17% | 0.21% | 0.26% | 0.01% | 1.30% | 0.19% | 0.24% | 0.02% |
| Lung | 0.90% | 0.20% | 0.27% | 0.01% | 1.08% | 0.11% | 0.93% | 0.11% |
| Spleen | 0.40% | 0.08% | 0.18% | 0.01% | 0.86% | 0.09% | 0.59% | 0.06% |
| Liver | 0.49% | 0.09% | 0.16% | 0.01% | 0.92% | 0.07% | 0.34% | 0.02% |
| Kidney-R | 8.03% | 1.46% | 2.54% | 0.14% | 10.24% | 0.52% | 5.73% | 0.20% |
| Kidney-L | 8.25% | 1.50% | 2.51% | 0.15% | 11.34% | 0.83% | 6.02% | 0.33% |
| Tumor | 0.83% | 0.14% | 0.51% | 0.02% | 0.78% | 0.10% | 0.54% | 0.03% |
| Muscle | 0.16% | 0.03% | 0.06% | 0.00% | 0.19% | 0.03% | 0.11% | 0.01% |
| Pancreas | 0.27% | 0.05% | 0.13% | 0.01% | 0.32% | 0.04% | 0.17% | 0.01% |

The present invention is not to be limited in scope by the specific embodiments described herein. Indeed, various modifications of the invention in addition to those described herein will become apparent to those skilled in the art from the foregoing description and the accompanying Figures. Such modifications are intended to fall within the scope of the appended claims. The complete disclosures of the various publications cited in the disclosure are incorporated herein by reference.

What is claimed is:

1. A compound of the formula (I):

$$\text{(B)}\!-\!\!\left[\text{NR}\!-\!\overset{\overset{\displaystyle S}{\|}}{C}\!\!-\!(\text{A})_n\!-\!P\right]_m \quad\text{(I)}$$

in which,

"B" is a saturated or unsaturated aliphatic or aromatic hydrocarbon backbone comprising 1–20 carbon atoms and, optionally, one or more heteroatoms selected from the group consisting of nitrogen, oxygen, phosphorus and sulfur;

"P" is a polypeptide comprising 2–100 amino acids, said polypeptide capable of targeting particular cells, tissues or organs of the body;

"A" may be the group —NR'—NR"— or the group —NR'—NR"—L— in which L may be an aliphatic or aromatic linker group comprising 1–12 carbon atoms and, optionally, one or more heteroatoms selected from the group consisting of nitrogen, oxygen, phosphorus and sulfur;

R' and R" may be the same or different and may be hydrogen or an aliphatic group comprising 1–6 carbon atoms and, optionally, one or more heteroatoms selected from the group consisting of nitrogen, oxygen, phosphorus and sulfur;

m is an integer $\geq 2$, provided that the groups R, R', R", L and "P" of a given —NR(CS)(A)$_n$—P chain may be the same or different from the groups R, R', R", L and "P" of another —NR(CS)(A)$_n$—P chain;

n is an integer $\geq 0$ and $\leq 2$;

or a pharmaceutically acceptable salt thereof.

2. The compound of claim 1 in which "A" is —NR'—NR'— when "P" is attached to "A" by a carboxylic acid group of said polypeptide.

3. The compound of claim 1 in which "A" is —NR'—NR'—L— when "P" is attached to "A" by an amino group of said polypeptide.

4. The compound of claim 1 in which "P" is attached to the thiocarbonyl group $$-\overset{\overset{\displaystyle S}{\|}}{C}-,$$

by an amino group of said polypeptide when n=0.

5. The compound of claim 1 in which at least one set of the groups R and R' forms a cyclic array with the thiourea group when n≠0.

6. The compound of claim 5 in which said cyclic array is covalently linked to said hydrocarbon backbone "B".

7. The compound of claim 1 in which a "P" of one —NR(CS) (A)$_n$—P chain is covalently linked to a "P" of another —NR(CS) (A)$_n$—P chain.

8. The compound of claim 1 in which a single "P" is shared by two or more —NR(CS) (A)$_n$—P chains, provided that said single "P" is comprised of three or more amino acids.

9. The compound of claim 1 in which said hydrocarbon backbone "B" comprises a phenyl group.

10. The compound of claim 1 in which said hydrocarbon backbone "B" comprises an alkylene chain of 2–6 carbon atoms.

11. The compound of claim 1 in which said hydrocarbon backbone "B" further comprises a functional group.

12. The compound of claim 11 in which said functional group is selected from the group consisting of hydroxy, amino, halo, epoxy, formyl, carboxylic acid, ester, amide, carboxylic acid hydrazide, semicarbazide, thiosemicarbazide, isothiocyanate, a double bond, and a triple bond.

13. The compound of claim 1 in which said polypeptide comprises 3–50 amino acids.

14. The compound of claim 1 in which said polypeptide comprises 3–25 amino acids.

15. The compound of claim 1 wherein "B" is a benzoic acid moiety further substituted at the 3- and 5-positions by —NR(CS)—P, wherein "P" is Neuromedin C.

16. The compound of claim 1 wherein said compound is a benzoic acid bisthiosemicarbazide derived from N-acetyl-Neuromedin C-hydrazide (SEQ. ID NO: 56).

17. The compound of claim 1 wherein said compound is benzoic acid bis-thiourea derived from Neuromedin C (SEQ. ID NO: 56).

18. The compound of claim 1 wherein said compound is lysine-alpha (epsilon-Neuromedin C-thiourea) Neuromedin C thiohydantoin.

19. The compound of claim 1 wherein "P" is somatostatin.

20. A pharmaceutical composition comprising the compound of claim 1 and a pharmaceutically acceptable carrier, subject.

21. A compound of the formula (III):

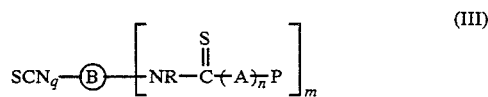

in which,
"B" is a saturated or unsaturated aliphatic or aromatic hydrocarbon backbone comprising 1–20 carbon atoms and, optionally, one or more heteroatoms selected from the group consisting of nitrogen, oxygen, phosphorus and sulfur;

"P" is a polypeptide comprising 2–100 amino acids, said polypeptide capable of targeting particular cells, tissues or organs of the body;

"A" may be the group —NR'—NR"— or the group —NR'—NR"—L— in which L may be an aliphatic or aromatic linker group comprising 1–12 carbon atoms and, optionally, one or more heteroatoms selected from the group consisting of nitrogen, oxygen, phosphorus and sulfur;

R, R', and R" may be the same or different and may be hydrogen or an aliphatic group comprising 1–6 carbon atoms and, optionally, one or more heteroatoms selected from the group consisting of nitrogen, oxygen, phosphorus and sulfur;

m is an integer ≧1, provided that the groups R, R', R", L and "P" of a given NR(CS)A$_n$—P chain may be the same or different from the groups R, R', R", L and "P" of another NR(CS)A$_n$—P chain;

n is an integer ≧0≦2;

q is an integer ≧1;

or a pharmaceutically acceptable salt thereof.

* * * * *